(12) United States Patent
Ohtsuki et al.

(10) Patent No.: US 9,163,276 B2
(45) Date of Patent: Oct. 20, 2015

(54) METHOD FOR FABRICATING STABLE-ISOTOPE-LABELED TARGET PEPTIDE FRAGMENT IN MASS SPECTROMETRY

(75) Inventors: Sumio Ohtsuki, Miyagi (JP); Tetsuya Terasaki, Miyagi (JP)

(73) Assignee: Tohoku University, Miyagi (JP)

(*) Notice: Subject to any disclaimer, the term of this patent is extended or adjusted under 35 U.S.C. 154(b) by 0 days.

(21) Appl. No.: 14/233,592

(22) PCT Filed: Jun. 18, 2012

(86) PCT No.: PCT/JP2012/003965
§ 371 (c)(1),
(2), (4) Date: Jan. 17, 2014

(87) PCT Pub. No.: WO2013/014853
PCT Pub. Date: Jan. 31, 2013

(65) Prior Publication Data
US 2014/0255966 A1    Sep. 11, 2014

(30) Foreign Application Priority Data
Jul. 22, 2011   (JP) .................. 2011-161351

(51) Int. Cl.
| C12Q 1/37 | (2006.01) |
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| G01N 33/68 | (2006.01) |
| G01N 30/72 | (2006.01) |
| G01N 30/88 | (2006.01) |

(52) U.S. Cl.
CPC .............. *C12Q 1/37* (2013.01); *G01N 33/6848* (2013.01); *G01N 30/7233* (2013.01); *G01N 2030/8827* (2013.01); *G01N 2458/15* (2013.01)

(58) Field of Classification Search
None
See application file for complete search history.

(56) References Cited

U.S. PATENT DOCUMENTS

| 2004/0072251 A1 | 4/2004 | Anderson |
| 2006/0014212 A1* | 1/2006 | Benkovic et al. .............. 435/7.1 |
| 2006/0154318 A1* | 7/2006 | Anderson .................... 435/7.92 |
| 2006/0211077 A1* | 9/2006 | Abel et al. ...................... 435/23 |
| 2012/0021446 A1* | 1/2012 | Ohtsuki et al. .................. 435/23 |

FOREIGN PATENT DOCUMENTS

| JP | 2003-192603 | 7/2003 |
| JP | 2004-028993 | 1/2004 |
| JP | 2004-077276 | 3/2004 |
| JP | 2004-533610 | 11/2004 |
| JP | 2006-300758 | 11/2006 |
| JP | 2010-085103 | 4/2010 |
| JP | 2010-197110 | 9/2010 |
| WO | 2007055166 A1 | 5/2007 |
| WO | 2010095365 A1 | 8/2010 |
| WO | 2013014853 A1 | 1/2013 |

OTHER PUBLICATIONS

Beynon et al. Multiplexed absolute quantification in proteomics using artificial QCAT proteins of concatenated signature peptides. Nature Methods, 2005. vol. 2, No. 8, pp. 587-589.*
Peptide Mapping section 2.2.55. European Pharmacopeia 5.0, 2005, pp. 82-86.*
Hoofnagle et al. Quantification of Thyroglobulin, a Low-Abundance Serum Protein, by Immunoaffinity Peptide Enrichment and Tandem Mass Spectrometry, Clinical Chemistry, 2008. vol. 54, No. 11, pp. 1796-1804.*
Baron, Andre T., et al., "A Preliminary Study of Serum Concentrations of Soluble Epidermal Growth Factor Receptor (sErbB1), Gonadotropins, and Steroid Hormones in Healthy Men and Women," Cancer Epidemiol Biomarkers Prev (Nov. 2001) 10:1175-1185.
Bhattacharjee, Arindam, et al., "Classification of human lung carcinomas by mRNA expression profiling reveals distinct adenocarcinoma subclasses," PNAS (Nov. 20, 2001) vol. 98, No. 24, pp. 13790-13795.
Gerber, Scott A., et al., "Absolute quantification of proteins and phosphoproteins from cell lysates by tandem MS," PNAS (Jun. 10, 2003) vol. 100, No. 12, pp. 6940-6945.

(Continued)

*Primary Examiner* — Marcela M Cordero Garcia
(74) *Attorney, Agent, or Firm* — Chainey P. Singleton; Edwin S. Flores; Chalker Flores, LLP

(57) ABSTRACT

An object of the present invention is to provide a method for producing a stable isotope-labeled target peptide fragment in mass spectrometry, which achieves inexpensive and convenient production. As a solution to attain the object, the stable isotope-labeled target peptide fragment in mass spectrometry is produced using a method comprising the steps of: expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments are linked in tandem; and a DNA encoding a peptide fragment for concentration measurement; subjecting the stable isotope-labeled protein to fragmentation treatment with trypsin to prepare a stable isotope-labeled peptide fragment for concentration measurement and stable isotope-labeled target peptide fragments; quantifying the stable isotope-labeled peptide fragment for concentration measurement using a liquid chromatograph-tandem mass spectrometer (LC/MS/MS); and calculating the concentration of the stable isotope-labeled target peptide fragment of each type from the quantification value of the stable isotope-labeled peptide fragment for concentration measurement.

19 Claims, 11 Drawing Sheets

(56) References Cited

OTHER PUBLICATIONS

Golub, et al., "Molecular Classification of Cancer: Class Discovery and Class Prediction by Gene Expression Monitoring," Science (Oct. 15, 1999) 286:531-537.

Michaud, Gregory A., et al., "Analyzing antibody specificity with whole proteome microarrays," Nature Biotechnology (Dec. 2003) vol. 21, No. 12, pp. 1509-1512.

Ramaswamy, Sridhar, et al., "Multiclass cancer diagnosis using tumor gene expression signatures," PNAS (Dec. 18, 2001) vol. 98, No. 26, pp. 15149-15154.

Yeang, Chen-Hsiang, et al., "Molecular classification of multiple tumor types," Bioinformatics (2001) vol. 17 Suppl., pp. S316-S322.

International Preliminary Report on Patentability [WIPO] PCT/JP2012/003965 dated Feb. 6, 2014.

Sakai, Kenjiro, et al., "Expression and Purification of Recombinant Reference Proteins for Evaluation of Absolute Quantification Method using LC-MS/MS," (Mar. 8, 2008)28PE-pm193.

Keiji Kito et al: "A Synthetic Protein Approach toward Accurate Mass Spectrometric Quantification of Component Stoichiometry of Multiprotein Complexes", Journal of Proteome Research, vol. 6, No. 2, Feb. 1, 2007, pp. 792-800.

Keiji Kito et al: "Mass Spectrometry-Based Approaches Toward Absolute Quantitative Proteomics", Current Genomics, vol. 9, No. 4, Jun. 1, 2008, pp. 263-274.

Nanavati Dhaval et al: "Stoichiometry and absolute quantification of proteins with mass spectrometry using fluorescent and isotope-labeled concatenated peptide standards", Molecular & Cellular Proteomics, American Society for Biochemistry and Molecular Biology, US, vol. 7, No. 2, Feb. 1, 2008, pp. 442-447.

Pratt Julie M et al: "Multiplexed absolute quantification for proteomics using concatenated signature peptides encoded by QconCAT genes",Nature Protocols, Nature Publishing Group, GB, vol. 1, No. 2, Jan. 1, 2006, pp. 1029-1043.

EP 1281 7205 Supplemenary European Search Report dated Feb. 2, 2015.

* cited by examiner

Figure 10

|  | 16-hour tryptic digestion | 3-hour digestion with Lys-C followed by 16-hour tryptic digestion |
|---|---|---|
|  | Mean ± SEM (fmol/μg protein) | Mean ± SEM (fmol/μg protein) |
| 4F2hc | 2.66 ± 0.10 | 2.97 ± 0.15 |
| mrp6 | 3.24 ± 0.03 | 3.37 ± 0.07 |
| abcg5 | 1.91 ± 0.22 | 1.86 ± 0.03 |
| abcg8 | 3.07 ± 0.10 | 3.22 ± 0.03 |
| oatp1 | 71.0 ± 5.39 | 71.9 ± 5.05 |
| mct1 | 21.9 ± 1.11 | 25.2 ± 0.59 |
| bsep | 8.34 ± 0.19 | 8.90 ± 0.47 |
| ntcp | 3.72 ± 0.32 | 26.2 ± 0.84*** |
| glut1 | 0.929 ± 0.06 | 1.00 ± 0.04 |
| bgt1 | 4.49 ± 0.23 | 5.02 ± 0.24 |
| Na/K ATPase | 28.5 ± 2.06 | 34.4 ± 2.44 |

Figure 14

| Name | | sequence | Peak area (counts) |
|---|---|---|---|
| Serum amylase | | SSDYFGNGR | 1.34E+06 |
| | | YVSDDGK | 5.21E+06 |
| Apo-A1 | | QGLLPVLESFK | 1.65E+06 |
| | | DLATVYVDVLK | 3.43E+06 |
| Apo-A2 | | SPELQAEAK | 2.23E+06 |
| Apo-B (48 + 100) | | IEIPLPFGGK | 7.77E+06 |
| | | EFOVPTFTIPK | 2.69E+06 |
| Apo-B100 | | NPNGYSFSIPVK | 5.29E+06 |
| | | NILPVYDK | 2.70E+06 |
| Apo-C2 | | TYLPAVDEK | 5.11E+06 |
| ApoC3 | | GWVTDGFSSLK | 6.81E+06 |
| Apo-E | | LGPLVEQGR | 7.02E+06 |
| GOT | Cytoplasmic | ITWSNPPAQGAR | 1.54E+06 |
| | | LALGDDSPALK | 3.22E+06 |
| | Mitochondrial | FVTVQTISGTGALR | 2.10E+05 |
| GPT | | ILVSGGGK | 2.65E+05 |
| | | TPSSWGR | 1.10E+06 |
| LDH | M subunit | LVIITAGAR | 7.92E+05 |
| | H subunit | IVVVTAGVR | 2.62E+05 |
| ALP | | FPFVALSK | 5.42E+05 |
| g-GTP | | LFQPSIQLAR | 7.85E+06 |
| | | GGLSVAVPGEIR | 1.04E+07 |
| ZTT | | EPQVYTLPPSR | 6.55E+06 |
| | | ALPAPIEK | 5.54E+06 |
| CHE | | NIAAFGGNPK | 4.31E+06 |
| | | FWTSFFPK | 3.46E+06 |
| CEA | | INGIPQQHTQVLFIAK | 1.90E+06 |
| PSA | | HSQPWQVLVASR | 4.65E+05 |
| CA125 | | LTSPVVTTSTR | 4.61E+06 |
| | | FPDIFSVASSR | 1.73E+06 |
| CA15-3 | | SSVPSSTEK | 4.39E+06 |
| | | ATTTPASK | 3.06E+06 |
| CYFRA | | ILGATIENSR | 4.57E+06 |
| PIVKA-II | | ANTFLEEVR | 4.26E+06 |
| HER 2 | | VLQGLPR | 9.20E+06 |
| | | GGVLIQR | 4.33E+06 |

Ratio of full length = Quantification value of peptide fragment B for concentration measurement / Quantification value of peptide fragment A for concentration measurement

METHOD FOR FABRICATING STABLE-ISOTOPE-LABELED TARGET PEPTIDE FRAGMENT IN MASS SPECTROMETRY

TECHNICAL FIELD

The present invention relates to a method for producing a stable isotope-labeled target peptide fragment for mass spectrometry and a method for quantifying a target protein in a sample.

BACKGROUND ART

With the recent progress of the human genome project, the pharmacogenomics, which involves individualizing drug susceptibility at the genetic level and applying the analysis results to pharmaceutical development, has been actively studied. Diagnosis capable of individualizing drug susceptibility enables so-called personalized therapy, which allows for appropriate medication at the early stage of treatment without carrying out medication by trial and error. Particularly, molecular target drugs with fewer adverse reactions compared with conventional anticancer agents have been actively developed in the field of cancer therapy and have also started to be used in clinical practice (see for example, patent document 1). The molecular target drugs are drugs that specifically act on targeted proteins. If protein expression levels in individual patients can be profiled to determine what target protein is highly expressed, appropriate personalized therapy may be planned and practiced.

Current testing methods mainly used in clinical practice, however, are intended for the detection of single proteins and cannot simultaneously detect a large number of different proteins. Most of these testing methods employ antibodies and therefore have difficulty in conducting specific quantification tests due to cross-reaction or the like (see for example, non-patent documents 1 and 2). In addition, different antibodies must be used on a protein basis and therefore require enormous labor and cost for detecting a large number of proteins. In order to solve such problems, microarray gene expression analysis methods have been developed recently and have led to the establishment of gene expression testing methods capable of quantifying the expression of various types of RNAs at once (see for example, non-patent documents 3 to 6). Many target proteins of the molecular target drugs, however, are membrane proteins expressed on cell membranes. Since membrane protein expression levels very poorly correlate with RNA expression levels, it is not considered that RNA expression profiles obtained by microarray analysis always agree with the protein expression profiles of patients. For these reasons, personalized therapy using molecular target drugs based on the results of microarray analysis is difficult to achieve. Thus, there is a strong demand for the establishment of a testing method capable of comprehensively quantifying actually expressed proteins.

In recent years, mass spectrometry has progressed drastically and has been applied to the detection or assay of various biological materials. Mass spectrometers (MS) having various functions have been developed so far, such as electrospray ionization mass spectrometers, liquid chromatograph-mass spectrometers (LC/MS) composed of a liquid chromatograph (LC) unit connected upstream of a mass spectrometer, tandem mass spectrometers (MS/MS) composed of two mass spectrometers connected in series, and liquid chromatograph-tandem mass spectrometers (LC/MS/MS) composed of a liquid chromatograph unit connected upstream of a tandem mass spectrometer. These apparatuses are widely used in the assay or quantification of biological materials (see for example, patent documents 2 to 4).

Mass spectrometry using stable isotope labels has been developed recently and used in the detection or assay of biological materials. This method involves quantifying proteins in a sample by mass spectrometry using stable isotope-labeled proteins. According to reports, this method has been used to quantify a diagnostic marker C-reactive protein (CRP) in the serum of rheumatism patients or β-amyloid in mammalian tissue samples and body fluids. In patent documents 5 to 7, the present inventors have modified such mass spectrometry and established a method for collectively determining the absolute expression levels of membrane proteins and metabolic enzymes using LC/MS/MS. This method employs, as internal standards, stable isotope-labeled target peptide fragments consisting of the same amino acid sequence as that of target peptide fragments contained in a target protein. As a result, the absolute amount of the target peptide fragments in a biological sample digested with trypsin can be quantified. This means that the expression level of the target protein can be determined. Unfortunately, the synthesis of stable isotope-labeled peptide fragments costs around 100,000 yen per type. Thus, cost reduction has been a challenge to the method.

PRIOR ART DOCUMENTS

Patent Documents

Patent Document 1: Japanese unexamined Patent Application Publication No. 2003-192603
Patent Document 2: Japanese unexamined Patent Application Publication No. 2004-28993
Patent Document 3: Japanese unexamined Patent Application Publication No. 2004-77276
Patent Document 4: Japanese unexamined Patent Application Publication (Translation of PCT Application) No. 2004-533610
Patent Document 5: International Publication No. WO 2007/055116
Patent Document 6: Japanese unexamined Patent Application Publication No. 2010-197110
Patent Document 7: Japanese unexamined Patent Application Publication No. 2010-85103

Non-Patent Documents

Non-patent Document 1: Baron et al., Cancer Epidemiology, Biomarkers & Prevention, 10: 1175-1185 (2001)
Non-patent Document 2: Michaud et al., Nature Biotechnology, 21: 1509-1512 (2003)
Non-patent Document 3: Golub et al., Science 286: 531-537 (1999)
Non-patent Document 4: Bhattacharjae et al., Proc. Natl. Acad. Sci. USA 98: 13790-13795 (2001)
Non-patent Document 5: Chen-Hsiang et al., Bioinformatics 17 (Suppl. 1): S316-S322 (2001)
Non-patent Document 6: Ramaswamy et al., Proc. Natl. Acad. Sci. USA 98: 15149-15154 (2001)

SUMMARY OF THE INVENTION

Object to be Solved by the Invention

An object of the present invention is [1] to provide a method for producing a stable isotope-labeled target peptide fragment for mass spectrometry, which achieves inexpensive and convenient production, and a method for quantifying a target protein in a sample using the stable isotope-labeled target peptide fragment. Another object of the present invention is [2] to provide an evaluation protein for mass spectrometry, which is used for evaluating protein digestion by trypsin. A further object of the present invention is [3] to provide a method for quantifying a target protein by mass spectrometry, which can accurately quantify a protein having a low rate of tryptic digestion. A further object of the present invention is [4] to provide a method for quantifying a target protein in mass spectrometry, which can improve quantitative performance for proteins.

Means to Solve the Object

In the course of diligent studies to attain the object [1], the present inventors found that a large number of target peptide fragments that allowed for highly sensitive quantification of a target protein serving as an index for the treatment or diagnosis of disease. The quantification of these target peptide fragments requires stable isotope-labeled target peptide fragments as internal standards. The present inventors considered that if stable isotope-labeled target peptide fragments could be expressed by in vitro protein synthesis and prepared without a further purification step, the stable isotope-labeled target peptide fragments could be produced more inexpensively and conveniently. In patent document 6, the present inventors disclose a peptide fragment for evaluation that does not have the same amino acid sequence as that of a known protein and has sufficient sensitivity in a mass spectrometer. This peptide fragment for evaluation is used to evaluate pretreatment efficiency in protein quantification using a mass spectrometer. The present inventors studied whether the peptide fragment for evaluation could be applied as a peptide fragment for concentration measurement in order to determine the concentrations of the stable isotope-labeled target peptide fragments. QIGDPTVPSGVK (SEQ ID NO: 1) was selected as the peptide fragment for concentration measurement from the peptide fragment for evaluation. A DNA encoding this peptide fragment for concentration measurement was conjugated with a tandemly linked DNA in which DNAs encoding 36 types of target peptide fragments were linked in tandem, to prepare a DNA conjugate, which was in turn used to prepare a stable isotope-labeled protein in a cell-free protein synthesis system having a stable isotope-labeled amino acid. Peptide fragments prepared by the fragmentation treatment of the stable isotope-labeled protein were assayed by LC/MS/MS. As a result, the stable isotope-labeled target peptide fragments were found to be able to be quantified, without the purification of the stable isotope-labeled protein, using the results of quantifying the peptide fragment for concentration measurement. Also, the stable isotope-labeled target peptide fragments were quantified by LC/MS/MS and consequently found to be able to be assayed with detection sensitivity of at least 10 fmol. In some cases, the stable isotope-labeled protein synthesized in a cell-free protein synthesis system may not be completely synthesized by a cause such as unoptimized synthesis conditions. Thus, in order to detect such cases, the present inventors studied a method for evaluating the complete synthesis of a stable isotope-labeled protein, comprising: adding the peptide fragment for concentration measurement (QIGDPTVPSGVK: SEQ ID NO: 1) to the amino terminus of the stable isotope-labeled protein, while adding another peptide fragment for concentration measurement (NVAPAGPTLK: SEQ ID NO: 2) to the carboxyl terminus thereof; and determining and comparing the concentrations of both the terminal peptide fragments for concentration measurement by LC/MS/MS. As a result of conducting studies using model protein 1 (MP1) (SEQ ID NO: 49) and model protein 2 (MP2) (SEQ ID NO: 50) as model proteins for verifying whether a full-length stable isotope-labeled protein was synthesized, the present inventors confirmed that, of synthesized model proteins, completely synthesized proteins can be quantified and evaluated. These findings led to the completion of the present invention.

In the course of diligent studies to attain the object [2], the present inventors also intend to prepare a protein for evaluation that enables evaluation of the complete digestion and fragmentation of proteins. In this process, the inventors used, as a reference, a protein for evaluation consisting of an amino acid sequence represented by SEQ ID NO: 6 containing 4 fragments each of 2 types of peptide fragments for evaluation (QIGDPTVPSGVK [SEQ ID NO: 1] and NVAPAGPTLK [SEQ ID NO: 2]) (second-generation evaluation protein), and studied whether the complete digestion of the second-generation evaluation protein can serve as an indicator for evaluating target analyte proteins as having been completely digested. The rate of digestion was analyzed as to 12 types of membrane proteins randomly selected from a large number of presumably indigestible cell membrane proteins (hereinafter, simply referred to as "membrane proteins"). As a result, 8 types of membrane proteins had a lower rate of digestion than that of the second-generation evaluation protein, i.e., only 4 types of membrane proteins (33%) could be evaluated as having been completely digested. Thus, the selection of the protein for evaluation was susceptible to improvement. In the course of this study, the present inventors paid attention on Na+/taurocholate cotransporting polypeptide (ntcp) having a particularly low rate of digestion. A peptide site (GIYDGDLK [SEQ ID NO: 7]) detected by LC/MS/MS in this ntcp protein was substituted by the peptide fragment for evaluation consisting of the amino acid sequence represented by QIGDPTVPSGVK (SEQ ID NO: 1) to construct a protein for evaluation (third-generation evaluation protein). As a result of conducting study again, this third-generation evaluation protein had a lower rate of digestion than that of 7 types of membrane proteins among 10 types of membrane proteins including the membrane proteins described above. Specifically, when the third-generation evaluation protein has been completely digested, 70% of the membrane proteins can be evaluated as having been also completely digested. Thus, use of the third-generation evaluation protein, compared with the second-generation evaluation protein, enables evaluation of digestion efficiency for a much larger proportion of target proteins. These findings led to the completion of the present invention.

The present inventors further conducted diligent studies on a protein digestion treatment method to attain the object [3]. It has heretofore been unknown that lysyl endopeptidase influences protein quantification values. The present inventors happened to use trypsin and lysyl endopeptidase in combination and consequently found that this combined use is effective for improving the fragmentation treatment efficiency of target proteins and thereby improving the quantification efficiency of the target proteins. These findings led to the completion of the present invention.

During diligent studies to attain the object [4], the present inventors further considered that the quantitative performance of target analyte proteins could be enhanced by the removal of impurities contained in a sample. SISCAPA is known as a method for removing impurities. This SISCAPA (stable isotope standards and capture by anti-peptide antibodies) method involves subjecting a protein sample to digestion treatment and then concentrating the resulting peptide fragments using antibodies. This method is limited by available antibodies, which must bind to the peptide fragments, and is therefore disadvantageous in terms of versatility. The concentration of proteins using antibodies before digestion treatment of a protein sample might carry impurities into the reaction solution. Although this was a matter of concern, the present inventors tried this experiment and consequently found that, surprisingly, this approach can improve quantitative performance. These findings led to the completion of the present invention.

Specifically, the present invention relates to: (1) a method for producing a stable isotope-labeled target peptide fragment for mass spectrometry, comprising the following steps (a) to (d): (a) expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments are linked in tandem; and a DNA encoding a peptide fragment for concentration measurement; (b) subjecting the stable isotope-labeled protein to digestion by trypsin to prepare a stable isotope-labeled peptide fragment for concentration measurement and stable isotope-labeled target peptide fragments; (c) quantifying the stable isotope-labeled peptide fragment for concentration measurement using a liquid chromatograph-tandem mass spectrometer (LC/MS/MS); and (d) calculating the concentration of the stable isotope-labeled target peptide fragments from the quantification value of the stable isotope-labeled peptide fragment for concentration measurement; (2) the production method according to (1), wherein the digestion by trypsin is digestion using trypsin and lysyl endopeptidase in combination; (3) the production method according to (1) or (2), wherein the peptide fragment for concentration measurement consists of an amino acid sequence represented by QIGDPTVPSGVK (SEQ ID NO: 1) or NVAPAGPTLK (SEQ ID NO: 2); (4) the production method according to any one of (1) to (3), wherein the DNA encoding a peptide fragment for concentration measurement is conjugated with the 5' end of the tandemly linked DNA, and a DNA encoding a peptide fragment for concentration measurement differing in amino acid sequence from the peptide fragment for concentration measurement encoded by the DNA conjugated with the 5' end of the tandemly linked DNA is conjugated with the 3' end of the tandemly linked DNA; and (5) the production method according to any one of (1) to (4), wherein the stable isotope-labeled protein is obtained by the expression of a DNA in which a portion of a DNA encoding ntcp protein consisting of an amino acid sequence represented by SEQ ID NO: 8 is substituted by the DNA conjugate.

The present invention also relates to (6) a method for quantifying a target protein in a sample, comprising the following steps (A) to (G): (A) expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments contained in target protein(s) are linked in tandem; and a DNA encoding a peptide fragment for concentration measurement; (B) subjecting the stable isotope-labeled protein to digestion by trypsin to prepare a stable isotope-labeled peptide fragment for concentration measurement and stable isotope-labeled target peptide fragments; (C) quantifying the stable isotope-labeled peptide fragment for concentration measurement using a liquid chromatograph-tandem mass spectrometer (LC/MS/MS); (D) calculating the concentration of the stable isotope-labeled target peptide fragments from the quantification value of the stable isotope-labeled peptide fragment for concentration measurement; (E) subjecting a sample comprising one or more types of target proteins to digestion by trypsin to prepare target peptide fragments; (F) using, as internal standards, the stable isotope-labeled target peptide fragments with the known concentration obtained by the steps (A) to (D) to quantify the target peptide fragments obtained in the step (E) using a liquid chromatograph-tandem mass spectrometer (LC/MS/MS); and (G) calculating the concentration of the target protein from the quantification value of the target peptide fragments.

The present invention further relates to (7) a method for quantifying a target protein in a sample, comprising the following steps (A') to (G'): (A') expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments contained in target protein(s) are linked in tandem; and a DNA encoding a peptide fragment for concentration measurement; (B') subjecting the stable isotope-labeled protein to digestion by trypsin to prepare a stable isotope-labeled peptide fragment for concentration measurement; (C') quantifying the stable isotope-labeled peptide fragment for concentration measurement using a liquid chromatograph-tandem mass spectrometer (LC/MS/MS); (D') calculating the concentration of the stable isotope-labeled target protein from the quantification value of the stable isotope-labeled peptide fragment for concentration measurement; (E') adding the stable isotope-labeled protein with the known concentration obtained in the step (D') to a sample comprising one or more types of target proteins, followed by digestion trypsin to prepare target peptide fragments and stable isotope-labeled target peptide fragments with the known concentration; (F') using, as internal standards, the stable isotope-labeled target peptide fragments with the known concentration obtained in the step (E') to quantify the target peptide fragments obtained in the step (E') using a liquid chromatograph-tandem mass spectrometer (LC/MS/MS); and (G') calculating the concentration of the target protein from the quantification value of the target peptide fragments.

The present invention further relates to (8) a method for quantifying a target protein in a sample, comprising the following steps (A") to (F"): (A") expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments contained in target protein(s) are linked in tandem; and a DNA encoding a peptide fragment for concentration measurement; (B") adding the stable isotope-labeled protein prepared in the step (A") to a sample comprising one or more types of target proteins, followed by digestion by trypsin to prepare target peptide fragments, stable isotope-labeled target peptide fragments, and a stable isotope-labeled peptide fragment for concentration measurement; (C") quantifying the stable isotope-labeled peptide fragment for concentration measurement using a liquid chromatograph-tandem mass spectrometer (LC/MS/MS); (D") calculating the concentration of the stable isotope-labeled target peptide fragments from the quantification value of the stable isotope-labeled peptide fragment for concentration measurement; (E") using, as internal standards, the stable isotope-labeled target peptide fragments with the known concentration obtained in the step (D") to quantify the target peptide fragments obtained in the step (B") using a liquid chromatograph-tandem mass spectrometer (LC/MS/MS); and (F'') calculating the concentration of the target protein from the quantification value of the target peptide fragments.

The present invention further relates to: (9) the quantification method according to any one of (6) to (8), further comprising a step (p) of, before the digestion by trypsin, contacting the target proteins with antibodies capable of specifically binding to the target proteins to purify the target proteins in advance; (10) the quantification method according to any one of (6) to (9), wherein the digestion by trypsin is digestion using trypsin and lysyl endopeptidase in combination; (11) the quantification method according to any one of (6) to (10), wherein the peptide fragment for concentration measurement consists of an amino acid sequence represented by QIGDPTVPSGVK (SEQ ID NO: 1) or NVAPAGPTLK (SEQ ID NO: 2); (12) the quantification method according to any one of (6) to (11), wherein the DNA encoding a peptide fragment for concentration measurement is conjugated with the 5' end of the tandemly linked DNA, and a DNA encoding a peptide fragment for concentration measurement differing in amino acid sequence from the peptide fragment for concentration measurement encoded by the DNA conjugated with the 5' end of the tandemly linked DNA is conjugated with the 3' end of the tandemly linked DNA; and (13) the quantification method according to any one of (6) to (12), wherein the stable isotope-labeled protein is obtained by the expression of a DNA in which a portion of a DNA encoding ntcp protein consisting of an amino acid sequence represented by SEQ ID NO: 8 is substituted by the DNA conjugate.

In an embodiment, the present invention provides a evaluation protein in which a portion of ntcp protein consisting of an amino acid sequence represented by SEQ ID NO: 8 is substituted by a peptide fragment for evaluation.

In another embodiment, the present invention provides a method (1) for quantifying a target protein in a sample, comprising the steps of: (a) subjecting a sample comprising one or more types of target proteins to digestion using trypsin and lysyl endopeptidase in combination to prepare target peptide fragments; and (b) using stable isotope-labeled target peptide fragments as internal standards to quantify the target peptide fragments using a liquid chromatograph-tandem mass spectrometer (LC/MS/MS).

In a further embodiment, the present invention provides: [1] a method (2) for quantifying a target protein in a sample, comprising the steps of: (a) contacting a sample comprising one or more types of target proteins with antibodies capable of specifically binding to the target proteins to purify the target proteins; (b) subjecting the target proteins to fragmentation treatment with trypsin to prepare target peptide fragments; and (c) using stable isotope-labeled target peptide fragments as internal standards to quantify the target peptide fragments using a liquid chromatograph-tandem mass spectrometer (LC/MS/MS); and [2] the quantification method (2) according to [1], wherein the fragmentation treatment with trypsin is fragmentation treatment using trypsin and lysyl endopeptidase in combination.

Effect of the Invention

The outsourcing of stable isotope-labeled target peptide fragments costs approximately 100,000 yen per type. By contrast, the production method of the present invention can synthesize stable isotope-labeled target peptide fragments at a cost of approximately 4,000 yen per type and is therefore excellent in economics. Moreover, the production method of the present invention can produce stable isotope-labeled target peptide fragments without a purification step and is therefore also excellent in convenience. Furthermore, the method of the present invention can identify and quantify a larger number of target proteins. As a result, even proteins on which no researcher can afford to work can be analyzed readily. This can contribute to the further evolution of pharmacokinetic research. Use of the evaluation protein of the present invention enables assay operation while confirming highly efficient digestion treatment of many target proteins including membrane proteins that exhibit low tryptic digestion treatment efficiency. The quantification method (1) of the present invention can enhance protein digestion treatment efficiency and can therefore quantify target proteins more accurately. The quantification method (2) of the present invention is not limited by antibodies, which must bind to target peptide fragments, and can therefore expand the range of choices for antibodies. Moreover, the quantification method (2) of the present invention can enhance quantitative performance by reducing the influence of impurities in a sample and can therefore quantify a trace amount of target proteins with a low concentration, for example, a trace amount of target proteins contained in blood or the like having a large volume.

BRIEF DESCRIPTION OF DRAWINGS

FIG. 10 is a diagram showing that the LC/MS/MS quantification values of 4F2 heavy chain (4F2hc), Multidrug resistance-associated protein-6 (mrp6), ATP-Cassette binding protein G5 (abcg5), ATP-Cassette binding protein G8 (abcg8), Organic Anion Transporting Polypeptide 1 (oatp1), mct1, bsep, ntcp, Glucose transporter 1 (glut1), Betaine/GABA (bgt1), and Na/K ATPase vary between 16-hour digestion with trypsin alone and 3-hour digestion with Lys-C followed by tryptic digestion.

FIG. 14 is a diagram showing the detection sensitivity of LC/MS/MS for 36 types of target peptide fragments as general diagnostic markers.

These 36 types of peptide fragments obtained by digestion treatment will be shown: SSDYFGNGR (SEQ ID NO: 12): serum amylase; IYVSDDGK (SEQ ID NO: 13): serum amylase QGLLPVLESFK (SEQ ID NO: 14): Apo-A1; DLATVYVDVLK (SEQ ID NO: 15): Apo-A1; SPELQAEAK (SEQ ID NO: 16): Apo-A2; IEIPLPFGGK (SEQ ID NO: 17): Apo-B(48+100); EFQVPTFTIPK (SEQ ID NO: 18): Apo-B(48+100); NPNGYSFSIPVK (SEQ ID NO: 19): Apo-B100; NIILPVYDK (SEQ ID NO: 20): Apo-B100; TYLPAVDEK (SEQ ID NO: 21): Apo-C2; GWVTDGFSSLK (SEQ ID NO: 22): Apo-C3; LGPLVEQGR (SEQ ID NO: 23): Apo-E; ITWSNPPAQGAR (SEQ ID NO: 24): GOT, cytoplasmic; LALGDDSPALK (SEQ ID NO: 25): GOT, cytoplasmic; FVTVQTISGTGALR (SEQ ID NO: 26): GOT, mitochondrial; ILVSGGGK (SEQ ID NO: 27): GPT; TPSSWGR (SEQ ID NO: 28): GPT; LVIITAGAR (SEQ ID NO: 29): LDH M subunit; IVVVTAGVR (SEQ ID NO: 30): LDH H subunit; FPFVALSK (SEQ ID NO: 31): ALP; LFQPSIQLAR (SEQ ID NO: 32): γ-GTP; GGLSVAVPGEIR (SEQ ID NO: 33): γ-GTP; EPQVYTLPPSR (SEQ ID NO: 34): ZTT; ALPAPIEK (SEQ ID NO: 35): ZTT; NIAAFGGNPK (SEQ ID NO: 36): CHE; FWTSFFPK (SEQ ID NO: 37): CHE; INGIPQQHTQVLFIAK (SEQ ID NO: 38): CEA; HSQPWQVLVASR (SEQ ID NO: 39): PSA; LTSPVVTTSTR (SEQ ID NO: 40): CA125; FPDIFSVASSR (SEQ ID NO: 41): CA125; SSVPSSTEK (SEQ ID NO: 42): CA15-3; ATTTPASK (SEQ ID NO: 43): CA15-3; ILGATIENSR (SEQ ID NO: 44): CYFRA; ANTFLEEVR (SEQ ID NO: 45): PIVKA-II; VLQGLPR (SEQ ID NO: 46): HER2; GGVLIQR (SEQ ID NO: 47): HER2.

Figure 15:
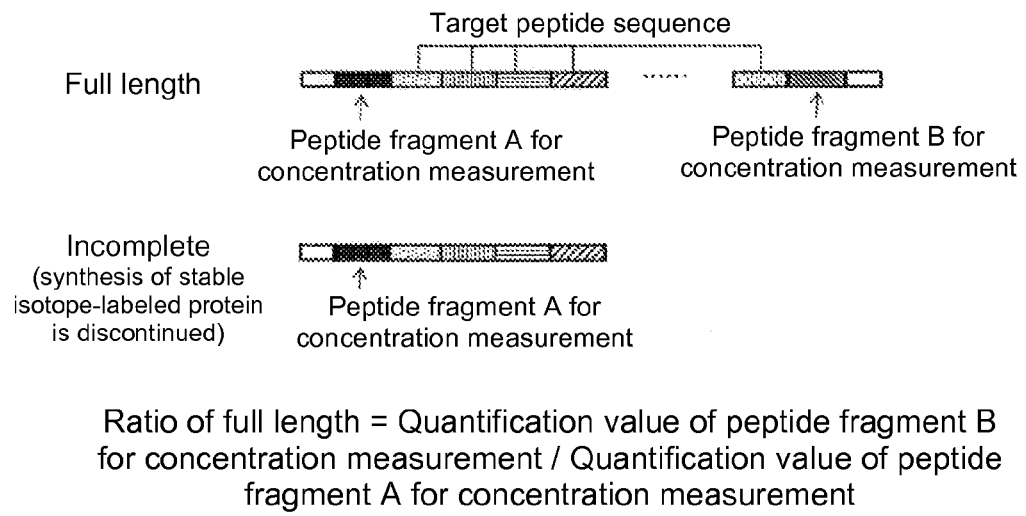

FIG. 15 is a diagram summarizing a method for evaluating the complete synthesis of the stable isotope-labeled protein of the present invention.

Figure 16:
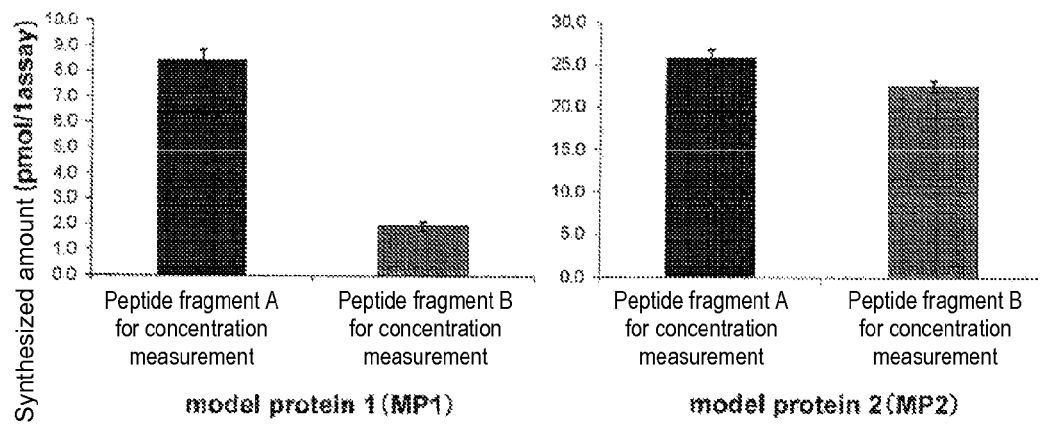

FIG. 16 is a diagram showing results of determining, by LC/MS/MS, the concentration of a peptide fragment for concentration measurement (QIGDPTVPSGVK: SEQ ID NO: 1) (in the diagram, "Peptide fragment A for concentration measurement") added to the amino termini of 2 types of proteins (MP1 and MP2) and the concentration of a peptide fragment for concentration measurement (NVAPAGPTLK: SEQ ID NO: 2) (in the diagram, "Peptide fragment B for concentration measurement") added to the carboxyl termini of these 2 types of proteins. The left graph shows the results obtained using MP1. The right graph shows the results obtained using MP2. Each value is indicated by mean±standard deviation (SEM) (n=4).

MODE OF CARRYING OUT THE INVENTION

The method for producing a stable isotope-labeled target peptide fragment in mass spectrometry according to the present invention is not particularly limited as long as the method comprises the following steps (a) to (d): (a) expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments are linked in tandem; and a DNA encoding a peptide fragment for concentration measurement; (b) subjecting the stable isotope-labeled protein to digestion by trypsin to prepare a stable isotope-labeled peptide fragment for concentration measurement and stable isotope-labeled target peptide fragments; (c) quantifying the stable isotope-labeled peptide fragment for concentration measurement using a liquid chromatograph-tandem mass spectrometer (LC/MS/MS); and (d) calculating the concentration of the stable isotope-labeled target peptide fragment of each type from the quantification value of the stable isotope-labeled peptide fragment for concentration measurement. In this context, the "stable isotope-labeled target peptide fragment in mass spectrometry" refers to a stable isotope-labeled target peptide fragment that is used as an internal standard for correcting variations in quantification value among assay runs in the quantification of a target peptide fragment to be quantified in mass spectrometry. The mass spectrometry of the present invention refers to an assay method using a mass spectrometer which involves converting a peptide fragment sample into gaseous ions (ionization) using ion sources, moving the generated ions in vacuum in an analysis unit, and separating the ions according to mass-to-charge ratios using electromagnetic force or difference in time of flight, followed by detection. For example, EI, CI, FD, FAB, MALDI, or ESI can be used as an ionization method using ion sources according to purposes. For example, magnetic deflection, quadrupole, ion trap, time-of-flight (TOF), or Fourier transform ion cyclotron resonance method can be appropriately selected as a method for separating the ionized peptide fragment sample in an analysis unit. Alternatively, tandem mass spectrometry (MS/MS) composed of two or more mass spectrometry techniques in combination may be used. Also, a sample containing target proteins may be fractionated using a liquid chromatograph (LC) or HPLC before introduction to the mass spectrometer. In addition, a detection unit or a data processing method can also be appropriately selected.

The method for quantifying a target protein in a sample according to the present invention is not particularly limited as long as the method is a method comprising the following steps (A) to (G): (A) expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments contained in target protein(s) are linked in tandem; and a DNA encoding a peptide fragment for concentration measurement; (B) subjecting the stable isotope-labeled protein to fragmentation treatment with trypsin to prepare a stable isotope-labeled peptide fragment for concentration measurement and stable isotope-labeled target peptide fragments; (C) quantifying the stable isotope-labeled peptide fragment for concentration measurement using a liquid chromatograph-tandem mass spectrometer (LC/MS/MS); (D) calculating the concentration of the stable isotope-labeled target peptide fragments of each type from the quantification value of the stable isotope-labeled peptide fragment for concentration measurement; (E) subjecting a sample comprising one or more types of target proteins to fragmentation treatment with trypsin to prepare target peptide fragments; (F) using, as internal standards, the stable isotope-labeled target peptide fragments with the known concentration obtained by the steps (A) to (D) to quantify the target peptide fragments obtained in the step (E) using a liquid chromatograph-tandem mass spectrometer (LC/MS/MS); and (G) calculating the concentration of the target protein of each type from the quantification value of the target peptide fragments, a method comprising the following steps (A') to (G'): (A') expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments contained in target protein(s) are linked in tandem; and a DNA encoding a peptide fragment for concentration measurement; (B') subjecting the stable isotope-labeled protein to fragmentation treatment with trypsin to prepare a stable isotope-labeled peptide fragment for concentration measurement; (C') quantifying the stable isotope-labeled peptide fragment for concentration measurement using a liquid chromatograph-tandem mass spectrometer (LC/MS/MS); (D') calculating the concentration of the stable isotope-labeled target protein from the quantification value of the stable isotope-labeled peptide fragment for concentration measurement; (E') adding the stable isotope-labeled protein with the known concentration obtained in the step (D') to a sample comprising one or more types of target proteins, followed by fragmentation treatment with trypsin to prepare target peptide fragments and stable isotope-labeled target peptide fragments with the known concentration; (F') using, as internal standards, the stable isotope-labeled target peptide fragments with the known concentration obtained in the step (E') to quantify the target peptide fragments obtained in the step (E') using a liquid chromatograph-tandem mass spectrometer (LC/MS/MS); and (G') calculating the concentration of the target protein of each type from the quantification value of the target peptide fragments, or a method comprising the following steps (A') to (F'): (A") expressing a DNA conjugate in a system having a stable isotope-labeled amino acid to thereby prepare a stable isotope-labeled protein, wherein the DNA conjugate comprises: a tandemly linked DNA in which two or more DNAs encoding one or more types of target peptide fragments contained in target protein(s) are linked in tandem; and a DNA encoding a peptide fragment for concentration measurement; (B") adding the stable isotope-labeled protein prepared in the step (A") to a sample comprising one or more types of target proteins, followed by fragmentation treatment with trypsin to prepare target peptide fragments, stable isotope-labeled target peptide fragments, and a stable isotope-labeled peptide fragment for concentration measurement; (C") quantifying the stable isotope-labeled peptide fragment for concentration measurement using a liquid chromatograph-tandem mass spectrometer (LC/MS/MS); (D") calculating the concentration of the stable isotope-labeled target peptide fragment of each type from the quantification value of the stable isotope-labeled peptide fragment for concentration measurement; (E") using, as internal standards, the stable isotope-labeled target peptide fragments with the known concentration obtained in the step (D") to quantify the target peptide fragments obtained in the step (B") using a liquid chromatograph-tandem mass spectrometer (LC/MS/MS); and (F") calculating the concentration of the target protein of each type from the quantification value of the target peptide fragments. Preferably, the method further comprises a step (p) of, before the fragmentation treatment with trypsin of one or more types of target proteins in the sample, contacting the target proteins with antibodies capable of specifically binding to the target proteins to purify the target proteins in advance. In this context, examples of the sample can specifically include, but not particularly limited to, cell membrane fraction samples obtained by subjecting, for example, cells, tissues, or blood collected from an organism to homogenization treatment using freeze-thawing, French press, glass beads, a homogenizer, an ultrasonic homogenizer, or the like or to fractionation treatment through differential centrifugation, sucrose density gradient centrifugation, or the like. The step (p) of purifying the target proteins according to the present invention is not particularly limited as long as the step involves a method of affinity-purifying each target protein through the use of antibody-antigen reaction between the target protein and its specific antibody. Examples of the affinity purification method can include immunoprecipitation using antibodies bound with protein beads (e.g., magnetic beads, Sepharose beads, or agarose beads covalently bound with protein A or protein G), and ELISA using antibodies immobilized on a solid phase such as plastics, silicon, or glass. ELISA can be a preferred example. The number of antibody types used is not particularly limited as long as the number is adapted to the number of target protein types.

The target protein of the present invention refers to a protein to be quantified. Examples of the target protein can include, but not particularly limited to, proteins serving as an index for the treatment or diagnosis of disease and can specifically include analyte proteins for general diagnosis, for example, serum amylase (Accession No. P04745, P04746, P19961), Apo-A1 (Accession No. P02647), Apo-A2 (Accession No. P02652), Apo-B(48+100) (Accession No. P04114), Apo-B100 (Accession No. P04114), Apo-C2 (Accession No. P02655), ApoC3 (Accession No. P02656), Apo-E (Accession No. P02649), GOT (cytoplasmic) (Accession No. P17174), GOT (mitochondrial) (Accession No. P00505), GPT (Accession No. Q8TD30), LDH_M (Accession No. P00338), LDH_H (Accession No. P07195), ALP (Accession No. P05186), γ-GTP (Accession No. P19440, P36268, or A6NGU5), ZTT (Accession No. P01857), CHE (Accession No. P06276), CEA (Accession No. P06731), PSA (Accession No. P07288), CA125 (Accession No. Q8WXI7), CA15-3 (Accession No. P15941), CYFRA (Accession No. P08727), PIVKA-II (Accession No. P00734), serum HER2 protein (Accession No. P04626), CRP (Accession No. P02741), AFP (Accession No. P02771), SCCA1 (Accession No. P29508), SCCA2 (Accession No. P48594), NSE (Accession No. P09104), ferritin_H (Accession No. P02794), ferritin_L (Accession No. P02792), elastase 1 (Accession No. Q14237), Pro-GRP (Accession No. P07492), and PAP (Accession No. P15309).

For example, 10 or more types, 20 or more types, 30 or more types, 35 or more types, or 40 or more types of target proteins, 2 to 50 types, 2 to 40 types, 2 to 36 types, 10 to 50 types, 10 to 40 types, 10 to 36 types, 20 to 50 types, 20 to 40 types, 20 to 36 types, 30 to 50 types, 30 to 40 types, 30 to 36 types, or 36 types of target proteins can be selected as two or more types of the target proteins.

The digestion by trypsin of the present invention can be any digestion for fragmenting proteins using trypsin. Preferred examples thereof can include treatment performed in a buffer solution for efficient tryptic treatment. The buffer solution may further contain other enzymes, chemicals, etc. The fragmentation treatment with trypsin is preferably fragmentation treatment using trypsin and lysyl endopeptidase in combination, because both arginine and lysine residues in the stable isotope-labeled protein or the target protein can be efficiently cleaved. The reaction conditions of trypsin are, for example, preferably 1 to 36 hours at 30° C. to 45° C., more preferably 16 to 24 hours at 36 to 37° C. The reaction conditions of lysyl endopeptidase are, for example, preferably 1 to 36 hours at 15 to 45° C., more preferably 2 to 4 hours at 15 to 25° C.

One or more types of target peptide fragments of the present invention are not particularly limited as long as the peptide fragments are selected according to: a step of selecting peptide fragments that satisfy the following essential criteria (1) to (3): (1) being a peptide fragment consisting of an amino acid sequence contained in the amino acid sequence of the target protein; (2) being a peptide fragment consisting of an amino acid sequence specific for the target protein; and (3) being a peptide fragment having a predicted elution time that falls within the range of 30 to 70 minutes when the predicted elution time is determined on the basis of an elution time parameter set for each amino acid by liquid chromatography under the following conditions (i) to (v): (i) HPLC: Agilent 1200 HPLC system (manufactured by Agilent Technologies, Inc.); (ii) column: XBridge BEH130 C18, 3.5 µm, 100×1.0 mm (manufactured by Waters Corp.); (iii) mobile phase: mobile phase A consisting of 0.1% formic acid/Milli Q water and mobile phase B consisting of 0.1% formic acid/acetonitrile; (iv) flow rate: 50 µL/min at 0 to 60 minutes and 100 µL/min at 60 to 90 minutes; and (v) concentration gradient: 99/1 (mobile phase A/mobile phase B) at 0 to 5 minutes, 99/1 (mobile phase A/mobile phase B)→50/50 (mobile phase A/mobile phase B) at 5 to 55 minutes, 100% mobile phase B at 56 to 58 minutes, and 99/1 (mobile phase A/mobile phase B) at 60 to 90 minutes; and a step of determining a total score on the basis of the following selection criteria (4) to (15) and preferentially selecting a peptide fragment having a high value of this total score: (4) giving score 10 to a peptide fragment having 80% or lower content of hydrophobic amino acids selected from tryptophan, tyrosine, valine, leucine, isoleucine, and phenylalanine, wherein the consecutiveness of the hydrophobic amino acids is less 10 amino acids; (5) giving score 3 to a peptide fragment having 4 to 30 amino acid residues; (6) giving score 10 to a peptide fragment that is not glycosylated according to annotation information of a protein database; (7) giving score 10 to a peptide fragment having no posttranslationally modified site except for quantification of posttranslationally modified proteins; (8) giving score 10 to a peptide fragment having no single-base polymorphism (SNP) site; (9) giving score 10 to a peptide fragment having a protease cleavage site other than arginine-arginine, arginine-lysine, lysine-arginine, or lysine-lysine; (10) giving score 10 to a peptide fragment having no transmembrane region in a determined or predicted protein structure; (11) giving score 10 to a peptide fragment free from methionine or cysteine; (12) giving score 1 to a peptide fragment free from tryptophan; (13) giving score 1 to a peptide fragment free from glutamic acid; (14) giving score 2 to a peptide fragment free from histidine; and (15) giving score 2 to a peptide fragment free from proline, and have a C-terminal arginine or lysine residue. More preferably, the peptide fragments have 50% or lower content of hydrophobic amino acids in the selection criterion (4) and have 6 to 16 amino acid residues in the selection criterion (5). The protein database in the selection criterion (6) is not particularly limited and can be any protein database known in the art, such as Protein Information Resource (PIR), SWISS-PROT & TrEMBL, Protein Research Foundation (PRF), NCBI Protein Database, or UniProt (http://www.uniprot.org/). Among them, NCBI Protein Database or UniProt (http://www.uniprot.org/) is preferred. Preferred examples of the "peptide fragment that is not glycosylated according to annotation information of a protein database" in the selection criterion (6) can specifically include peptide fragments free from a sequence asparagine-X-serine, asparagine-X-threonine, or asparagine-X-cysteine wherein X represents an amino acid other than proline.

The elution time parameter for each amino acid in the essential criterion (3) is not particularly limited as long as the parameter is set on the basis of elution time data obtained by the liquid chromatography separation of a peptide fragment consisting of a known amino acid sequence under the following conditions (i) to (v): (i) HPLC: Agilent 1200 HPLC system (manufactured by Agilent Technologies, Inc.); (ii) column: XBridge BEH130 C18, 3.5 µm, 100×1.0 mm (manufactured by Waters Corp.); (iii) mobile phase: mobile phase A consisting of 0.1% formic acid/Milli Q water and mobile phase B consisting of 0.1% formic acid/acetonitrile; (iv) flow rate: 50 µL/min at 0 to 60 minutes and 100 µL/min at 60 to 90 minutes; and (v) concentration gradient: 99/1 (mobile phase A/mobile phase B) at 0 to 5 minutes, 99/1 (mobile phase A/mobile phase B)→50/50 (mobile phase A/mobile phase B) at 5 to 55 minutes, 100% mobile phase B at 56 to 58 minutes, and 99/1 (mobile phase A/mobile phase B) at 60 to 90 minutes. More specifically, preferred examples of the elution time parameter can include −0.672 for alanine (A), +1 for cysteine (C), +0.769 for aspartic acid (D), +0.081 for glutamic acid (E), +16.309 for phenylalanine (F), −0.251 for glycine (G), −2.995 for histidine (H), +7.763 for isoleucine (I), −3.201 for lysine (K), +10.468 for leucine (L), +8.313 for methionine (M), −1 for asparagine (N), +2.195 for proline (P), −1 for glutamine (Q), −0.013 for arginine (R), −2.181 for serine (S), +4.215 for threonine (T), +6.422 for valine (V), +18.65 for tryptophan (W), and +7.37 for tyrosine (Y). The elution time of each peptide fragment in liquid chromatography under the conditions (i) to (v) can be calculated on the basis of the elution time parameters for these amino acids.

The "peptide fragment having a predicted elution time that falls within the range of 30 to 70 minutes" in the essential criterion (3) means a peptide fragment predicted to be eluted at an elution time ranging from 30 to 70 minutes calculated on the basis of the elution time parameter for each amino acid by liquid chromatography under the following conditions (i) to (v): (i) HPLC: Agilent 1200 HPLC system (manufactured by Agilent Technologies, Inc.); (ii) column: XBridge BEH130 C18, 3.5 µm, 100×1.0 mm (manufactured by Waters Corp.); (iii) mobile phase: mobile phase A consisting of 0.1% formic acid/Milli Q water and mobile phase B consisting of 0.1% formic acid/acetonitrile; (iv) flow rate: 50 µL/min at 0 to 60 minutes and 100 µL/min at 60 to 90 minutes; and (v) concentration gradient: 99/1 (mobile phase A/mobile phase B) at 0 to 5 minutes, 99/1 (mobile phase A/mobile phase B)→50/50 (mobile phase A/mobile phase B) at 5 to 55 minutes, 100% mobile phase B at 56 to 58 minutes, and 99/1 (mobile phase A/mobile phase B) at 60 to 90 minutes. In this context, the "elution time" means a time required from introduction to a liquid chromatograph to discharge therefrom, i.e., a retention time in a column for liquid chromatography. The predicted elution time of the peptide fragment is not particularly limited and can be within the range of 30 to 70 minutes. The predicted elution time may be, for example, 30 to 65 minutes, 30 to 60 minutes, 35 to 70 minutes, 35 to 65 minutes, 35 to 60 minutes, 40 to 70 minutes, 40 to 65 minutes, or 40 to 60 minutes and is preferably 40 to 60 minutes.

Specific examples of the target peptide fragments can include peptide fragments each consisting of an amino acid sequence represented by any of SEQ ID NOs: 13 to 48 for quantifying analyte proteins for general diagnosis. More specifically, examples of the target peptide fragments can include: SSDYFGNGR (SEQ ID NO: 13) and IYVSDDGK (SEQ ID NO: 14) which are partial sequences of serum amylase (Accession No. P04745, P04746, or P19961); QGLLPVLESFK (SEQ ID NO: 15) and DLATVYVDVLK (SEQ ID NO: 16) which are partial sequences of Apo-A1 (Accession No. P02647); SPELQAEAK (SEQ ID NO: 17) which is a partial sequence of Apo-A2 (Accession No. P02652); IEIPLPFGGK (SEQ ID NO: 18) and EFQVPTFTIPK (SEQ ID NO: 19) which are partial sequences of Apo-B(48+100) (Accession No. P04114); NPNGYSFSIPVK (SEQ ID NO: 20) and NIILPVYDK (SEQ ID NO: 21) which are partial sequences of Apo-B100 (Accession No. P04114); TYLPAVDEK (SEQ ID NO: 22) which is a partial sequence of Apo-C2 (Accession No. P02655); GWVTDGFSSLK (SEQ ID NO: 23) which is a partial sequence of ApoC3 (Accession No. P02656); LGPLVEQGR (SEQ ID NO: 24) which is a partial sequence of Apo-E (Accession No. P02649); ITWSNPPAQGAR (SEQ ID NO: 25) and LALGDDSPALK (SEQ ID NO: 26) which are partial sequences of GOT (cytoplasmic) (Accession No. P17174); FVTVQTISGTGALR (SEQ ID NO: 27) which is a partial sequence of GOT (mitochondrial) (Accession No. P00505); ILVSGGGK (SEQ ID NO: 28) and TPSSWGR (SEQ ID NO: 29) which are partial sequences of GPT (Accession No. Q8TD30); LVIITAGAR (SEQ ID NO: 30) which is a partial sequence of LDH_M (Accession No. P00338); IVVVTAGVR (SEQ ID NO: 31) which is a partial sequence of LDH_H (Accession No. P07195); FPFVALSK (SEQ ID NO: 32) which is a partial sequence of ALP (Accession No. P05186); LFQPSIQLAR (SEQ ID NO: 33) and GGLSVAVPGEIR (SEQ ID NO: 34) which are partial sequences of γ-GTP (Accession No. P19440 or P36268); EPQVYTLPPSR (SEQ ID NO: 35) and ALPAPIEK (SEQ ID NO: 36) which are partial sequences of ZTT (Accession No. P01857); NIAAFGGNPK (SEQ ID NO: 37) and FWTSFFPK (SEQ ID NO: 38) which are partial sequences of CHE (Accession No. P06276); INGIPQQHTQVLFIAK (SEQ ID NO: 39) which is a partial sequence of CEA (Accession No. P06731); HSQPWQVLVASR (SEQ ID NO: 40) which is a partial sequence of PSA (Accession No. P07288); LTSPVVTTSTR (SEQ ID NO: 41) and FPDIFSVASSR (SEQ ID NO: 42) which are partial sequences of CA125 (Accession No. Q8WXI7); SSVPSSTEK (SEQ ID NO: 43) and ATTTPASK (SEQ ID NO: 40) which are partial sequences of CA15-3 (Accession No. P15941); ILGATIENSR (SEQ ID NO: 45) which is a partial sequence of CYFRA (Accession No. P08727); ANTFLEEVR (SEQ ID NO: 46) which is a partial sequence of PIVKA-II (Accession No. P00734); and VLQGLPR (SEQ ID NO: 47) and GGVLIQR (SEQ ID NO: 48) which are partial sequences of serum HER2 protein (Accession No. P04626).

Two or more types of the target peptide fragments can be target peptide fragments corresponding to the number of types of target proteins to be quantified and the types of the target proteins. For example, 10 or more types, 20 or more types, 30 or more types, 35 or more types, or 40 or more types of target peptide fragments, 2 to 50 types, 2 to 40 types, 2 to 36 types, 10 to 50 types, 10 to 40 types, 10 to 36 types, 20 to 50 types, 20 to 40 types, 20 to 36 types, 30 to 50 types, 30 to 40 types, 30 to 36 types, or 36 types of target peptide fragments can be selected.

The tandemly linked DNA of the present invention refers to a DNA in which DNAs encoding target peptide fragments are linked at the same transcriptional orientation as each other. The tandemly linked DNA of the present invention is not particularly limited and can be any DNA in which two or more DNAs encoding target peptide fragments are linked in tandem. In this context, examples of these two or more DNAs linked can include 10 or more, 20 or more, 30 or more, 35 or more, or 40 or more linked DNAs, 2 to 50, 2 to 40, 2 to 36, 10 to 50, 10 to 40, 10 to 36, 20 to 50, 20 to 40, 20 to 36, 30 to 50, 30 to 40, 30 to 36, or 36 linked DNAs. The DNAs encoding target peptide fragments can be appropriately selected on the basis of amino acid sequence information about the target peptide fragments. Alternatively, the tandemly linked DNA of the present invention may be a DNA in which DNAs encoding target peptide fragments are linked in tandem between which a linker DNA is inserted. In this context, the linker DNA is not particularly limited and can be any amino acid sequence-encoding DNA designed so as not to cause frame shift in the target peptide fragments and not to have a stop codon. In consideration of the influence of amino acids near a tryptic cleavage site on cleavage efficiency, preferred examples of the linker DNA can include a DNA encoding amino acids flanking each target peptide fragment in the target protein. Also, the 3'-terminal codon in the linker DNA preferably encodes an arginine or lysine residue for allowing fragmentation treatment with trypsin to cleave the target peptide fragment from the linker DNA-derived peptide fragment. The number of bases in the linker DNA is not particularly limited and can be, for example, 3 bases, 6 bases, 9 bases, or 12 bases.

The peptide fragment for concentration measurement of the present invention refers to a peptide fragment that is quantified by mass spectrometry in order to measure the concentrations of stable isotope-labeled target peptide fragments. The peptide fragment for concentration measurement of the present invention is not particularly limited as long as the peptide fragment has 3 to 20 amino acid residues, has a C-terminal arginine residue (R) or lysine residue (K), has neither arginine nor lysine residues at a site other than the C terminus, differs in amino acid sequence from naturally occurring proteins and their variants, and can be detected by LC/MS/MS. The peptide fragment for concentration measurement of the present invention is preferably a peptide fragment that has 8, 10, or 12 amino acid residues and contains 1 or 2 proline or glycine residues without histidine. Specific examples thereof can include QIGDPTVPSGVK (SEQ ID NO: 1), NVAPAGPTLK (SEQ ID NO: 2), VGAPGVPALK (SEQ ID NO: 3), and DAPGSGLK (SEQ ID NO: 4). Among them, QIGDPTVPSGVK (SEQ ID NO: 1) or NVAPAGPTLK (SEQ ID NO: 2) can be a preferred example. The peptide fragment for concentration measurement of the present invention can be quantified distinctively from naturally occurring peptide fragments and as such, can be added to a sample for use. A DNA encoding the peptide fragment for concentration measurement of the present invention can be appropriately selected on the basis of amino acid sequence information about the peptide fragment for concentration measurement.

The DNA conjugate of the present invention refers to a DNA in which the tandemly linked DNA of the present invention is conjugated with the DNA encoding the peptide fragment for concentration measurement. The DNA encoding the peptide fragment for concentration measurement of the present invention may be conjugated with either 5' or 3' end of the tandemly linked DNA. In the case of evaluating the complete protein synthesis of a stable isotope-labeled protein, preferably, the DNA encoding the peptide fragment for concentration measurement is conjugated with the 5' end of the tandemly linked DNA, and a DNA encoding a peptide fragment for concentration measurement differing in amino acid sequence from the peptide fragment for concentration measurement encoded by the DNA conjugated with the 5' end of the tandemly linked DNA is conjugated with the 3' end of the tandemly linked DNA. In this case, the peptide fragments for concentration measurement used are not particularly limited and can each be any peptide fragment for concentration measurement of the present invention. Preferred examples thereof can include QIGDPTVPSGVK (SEQ ID NO: 1) and NVAPAGPTLK (SEQ ID NO: 2). The complete protein synthesis of a stable isotope-labeled protein can be evaluated on the basis of a concentration ratio between the calculated concentrations of the peptide fragment for concentration measurement encoded by the DNA conjugated with the 5' end of the tandemly linked DNA and the peptide fragment for concentration measurement encoded by the DNA conjugated with the 3' end thereof.

The stable isotope-labeled amino acid of the present invention can be any amino acid containing a stable isotope element and is not particularly limited as long as the amino acid contains any one or more stable isotope labels selected from, for example, $^{15}N$, $^{13}C$, $^{18}O$, and $^{2}H$ and is labeled with the stable isotopes. The amino acid to be stable isotope-labeled is not particularly limited as long as the amino acid is any of 20 types of L-amino acids (L-alanine, L-arginine, L-aspartic acid, L-glutamic acid, glycine, L-histidine, L-isoleucine, L-leucine, L-lysine, L-methionine, L-phenylalanine, L-proline, L-serine, L-threonine, L-tyrosine, L-valine, L-tryptophan, L-cysteine, L-asparagine, and L-glutamine) and is contained in each target peptide fragment. The amino acid is preferably L-arginine and/or L-lysine which serve as a tryptic cleavage site.

The stable isotope-labeled protein of the present invention may be a tag-containing stable isotope-labeled protein that is obtained by the expression of a DNA comprising the DNA conjugate as well as a DNA encoding a tag sequence for protein purification, for example, a transport signal sequence, glutathione-S-transferase (GST), or histidine. The stable isotope-labeled protein of the present invention is preferably a stable isotope-labeled protein that is obtained by the expression of a DNA free from the DNA encoding a tag sequence for protein purification. Further examples of the stable isotope-labeled protein of the present invention can specifically include a stable isotope-labeled protein obtained by the expression of a DNA in which a portion of a DNA encoding ntcp protein consisting of an amino acid sequence represented by SEQ ID NO: 8 is substituted by the DNA conjugate. In this context, a portion of the DNA encoding ntcp protein is preferably a DNA encoding an LC/MS/MS-quantifiable amino acid sequence in the ntcp protein. Specific examples thereof can include a DNA encoding an amino acid sequence represented by GIYDGDLK (SEQ ID NO: 7).

The stable isotope-labeled protein of the present invention can be prepared by the expression of the DNA conjugate of the present invention in a system having a stable isotope-labeled amino acid. Examples of the system having a stable isotope-labeled amino acid can include a cell-free protein synthesis system and a live-cell protein synthesis system having the stable isotope-labeled amino acid. Specifically, the stable isotope-labeled protein of the present invention can be prepared from the DNA conjugate of the present invention by protein synthesis in a cell-free protein synthesis system with the stable isotope-labeled amino acid as well as stable isotope-unlabeled amino acids as materials or by the culture of cells transformed with the DNA conjugate of the present invention in the presence of the stable isotope-labeled amino acid in a live-cell protein synthesis system.

The expression of the stable isotope-labeled protein of the present invention using the cell-free protein synthesis system can be performed using the DNA conjugate of the present invention, the stable isotope-labeled amino acid, stable isotope-unlabeled amino acids necessary for stable isotope-labeled protein synthesis, a cell extract for cell-free protein synthesis, energy sources (high-energy phosphate bond-containing materials such as ATP, GTP, or creatine phosphate), etc. Reaction conditions such as temperature and time can be appropriately set to the optimum conditions. For example, the temperature is 20 to 40° C., preferably 23 to 37° C. The reaction time is 1 to 24 hours, preferably 10 to 20 hours. The "cell extract for cell-free protein synthesis" refers to an extract from plant cells, animal cells, fungal cells, or bacterial cells containing components necessary for a transcription system or a transcription-translation system involved in protein synthesis, such as ribosomes and tRNAs. Specific examples thereof can include cell extracts from *E. coli*, wheat germ, rabbit reticulocytes, mouse L-cells, Ehrlich ascites cancer cells, HeLa cells, CHO cells, or budding yeast. This cell extract can be prepared according to a method described in, for example, Pratt, J. M. et al., Transcription and translation—a practical approach (1984), pp. 179-209. Specifically, the cells are subjected to homogenization treatment using French press, glass beads, an ultrasonic homogenizer, or the like. A buffer solution containing several types of salts is added thereto for solubilization of protein components or ribosomes, and the mixture is homogenized and centrifuged to precipitate insoluble components.

Alternatively, the expression of the stable isotope-labeled protein of the present invention using the cell-free protein synthesis system may be performed appropriately using a commercially available kit such as Premium Expression Kit (manufactured by CellFree Sciences Co., Ltd) with a wheat germ extract, RTS 100, *E. coli* HY Kit (manufactured by Roche Applied Science) with an *E. coli* extract, or Musaibokun Quick (manufactured by Taiyo Nippon Sanso Corp.). The expressed stable isotope-labeled protein, when insoluble, may be appropriately solubilized using a protein denaturant such as guanidine hydrochloride or urea. After the solubilization, the concentration of the protein denaturant is adjusted to prevent the inhibition of fragmentation treatment with trypsin. The stable isotope-labeled protein may be prepared by further fractionation treatment through differential centrifugation, sucrose density gradient centrifugation, or the like or purification treatment using affinity columns, ion-exchange chromatography, or the like. In a preferred example, the stable isotope-labeled protein is prepared without this fractionation treatment or purification treatment.

On the other hand, the expression of the stable isotope-labeled protein of the present invention using the live-cell protein synthesis system can be performed by the culture of live cells transformed with the DNA conjugate of the present invention in a culture solution containing nutrients, antibiotics, the stable isotope-labeled amino acid, the stable isotope-unlabeled amino acids necessary for stable isotope-labeled protein synthesis, etc. In this context, the live cells are not particularly limited as long as the live cells can express the DNA conjugate of the present invention. Examples thereof can include live cells of mammalian cell lines (e.g., Chinese hamster ovary (CHO) cells), *E. coli*, yeast cells, insect cells, and plant cells. *E. coli* is preferred in terms of convenience or cost-benefit performance. The DNA conjugate of the present invention can be expressed by: incorporating the DNA conjugate to an expression vector designed so as to permit expression in selected live cells by a gene recombination technique; and introducing this expression vector to the live cells. The live cells can be transformed with the DNA conjugate of the present invention by a method suitable for the live cells used. Examples of the method can include electroporation, heat shock method, calcium phosphate method, lipofection, DEAE dextran method, microinjection, particle gun method, a method using viruses, and a method using a commercially available transfection reagent such as FuGENE® 6 Transfection Reagent (manufactured by Roche Applied Science) or Lipofectamine 2000 Reagent (manufactured by Invitrogen Corp.).

The stable isotope-labeled protein of the present invention expressed in the live-cell protein synthesis system can be prepared by the homogenization treatment or extraction treatment of the live cells containing the stable isotope-labeled protein. Examples of the homogenization treatment can include physical homogenization treatment using freeze-thawing, French press, glass beads, a homogenizer, an ultrasonic homogenizer, or the like. Examples of the extraction treatment can include extraction treatment with a protein denaturant such as guanidine hydrochloride or urea. The stable isotope-labeled protein may be prepared by further fractionation treatment through differential centrifugation, sucrose density gradient centrifugation, or the like or purification treatment using affinity columns, ion-exchange chromatography, or the like. In a preferred example, the stable isotope-labeled protein is prepared without this fractionation treatment or purification treatment.

The stable isotope-labeled peptide fragment for concentration measurement of the present invention can be quantified on the basis of a prepared calibration curve using a liquid chromatograph-tandem mass spectrometer (LC/MS/MS). The preparation of the calibration curve and the quantification based on the calibration curve can be performed as follows.

(Preparation of Calibration Curve for Quantifying Stable Isotope-Labeled Peptide Fragment for Concentration Measurement)

The calibration curve can be prepared by: adding a defined amount of an internal standard peptide fragment for concentration measurement with a known concentration to stable isotope-labeled peptide fragments for concentration measurement with several series of known concentrations; subjecting the mixture to mass spectrometry using LC/MS/MS; and calculating the area ratio or peak height ratio between the MS spectra of the stable isotope-labeled peptide fragment for concentration measurement with each concentration and the unlabeled peptide fragment for concentration measurement. Preferably, the amounts of the stable isotope-labeled peptide fragments for concentration measurement fall within a linear measurement range of the mass spectrometer. The stable isotope-labeled peptide fragments for concentration measurement with known concentrations used may be chemically synthesized by appropriate means such as F-moc method (Amblard., et al. Methods Mol. Biol. 298: 3-24 (2005)) using stable isotope element-labeled amino acids. Alternatively, the stable isotope-labeled peptide fragments for concentration measurement with known concentrations used may be obtained by the production method of the present invention. Also, the peptide fragment for concentration measurement with a known concentration can be produced by a general chemical synthesis method. Any of a stepwise elongation method which involves sequentially linking amino acids one by one on the basis of amino acid sequence information to elongate the chain and a fragment condensation method which involves synthesizing in advance fragments each consisting of several amino acids and subsequently coupling these fragments through reaction can be adopted as the peptide synthesis method.

(Quantification of Stable Isotope-Labeled Peptide Fragment for Concentration Measurement on the Basis of Calibration Curve)

A defined amount of an internal standard peptide fragment for concentration measurement with a known concentration is added into a peptide sample containing the stable isotope-labeled peptide fragment for concentration measurement of the present invention prepared by the fragmentation treatment with trypsin of the stable isotope-labeled protein. The mixture is subjected to mass spectrometry using LC/MS/MS. The area ratio of the mass spectrum of the stable isotope-labeled peptide fragment for concentration measurement/the mass spectrum of the peptide fragment for concentration measurement is calculated. The stable isotope-labeled peptide fragment for concentration measurement of the present invention can be quantified from the area ratio using the calibration curve. The peptide fragment for concentration measurement with a known concentration can be produced by a general chemical synthesis method. Any of a stepwise elongation method which involves sequentially linking amino acids one by one on the basis of amino acid sequence information to elongate the chain and a fragment condensation method which involves synthesizing in advance fragments each consisting of several amino acids and subsequently coupling these fragments through reaction can be adopted as the peptide synthesis method.

The concentration of the stable isotope-labeled protein can be calculated from the quantification value (M) of the stable isotope-labeled peptide fragment for concentration measurement of the present invention. Also, the concentration of the stable isotope-labeled target peptide fragment of each type can be calculated by substituting the quantification value (M) of the stable isotope-labeled peptide fragment for concentration measurement and the number of the stable isotope-labeled target peptide fragments contained in the stable isotope-labeled protein into the expression (Quantification value [M] of the stable isotope-labeled peptide fragment for concentration measurement)×(The number of the stable isotope-labeled target peptide fragments contained in the stable isotope-labeled protein). The stable isotope-labeled target peptide fragments with the known concentration of the present invention thus obtained can be used as internal standards for quantifying the target peptide fragment of the present invention.

The target peptide fragment of the present invention can be quantified on the basis of a prepared calibration curve using a liquid chromatograph-tandem mass spectrometer (LC/MS/MS). The preparation of the calibration curve and the quantification based on the calibration curve can be performed as follows.

(Preparation of Calibration Curve for Quantifying Target Peptide Fragment)

The calibration curve can be prepared by: adding a defined amount of an internal standard stable isotope-labeled target peptide fragment with the known concentration of the present invention to target peptide fragments with several series of known concentrations; subjecting the mixture to mass spectrometry using LC/MS/MS; and calculating the area ratio or peak height ratio between the MS spectra of the target peptide fragment with each concentration and the stable isotope-labeled target peptide fragment of the present invention. Preferably, the amounts of the target peptide fragments fall within a linear measurement range of the mass spectrometer. The target peptide fragment with the known concentration can be produced by a general chemical synthesis method. Any of a stepwise elongation method which involves sequentially linking amino acids one by one on the basis of amino acid sequence information to elongate the chain and a fragment condensation method which involves synthesizing in advance fragments each consisting of several amino acids and subsequently coupling these fragments through reaction can be adopted as the peptide synthesis method. Alternatively, the target peptide fragment with the known concentration may be isolated by: expressing the DNA conjugate of the present invention in a system having no stable isotope-labeled amino acid to prepare a protein; and treating this protein with trypsin or the like. The concentration of this target peptide fragment can be calculated on the basis of the quantification value of the peptide fragment for concentration measurement.

(Quantification of Target Peptide Fragment on the Basis of Calibration Curve)

A defined amount of an internal standard stable isotope-labeled target peptide fragment with the known concentration of the present invention is added into a peptide sample containing the target peptide fragment of the present invention prepared by the fragmentation treatment with trypsin of a sample containing the target protein. The mixture is subjected to mass spectrometry using LC/MS/MS. The area ratio of the mass spectrum of the target peptide fragment/the mass spectrum of the stable isotope-labeled target peptide fragment is calculated. The target peptide fragment can be quantified from the area ratio by calculation using the calibration curve.

The concentration of the target protein can be calculated by substituting the calculated quantification value of the target peptide fragment and the number of the target peptide fragments contained in the target protein into the expression (Quantification value [M] of the target peptide fragment)/(The number of the target peptide fragments contained in the target protein).

The evaluation protein of the present invention refers to a protein to be quantified by mass spectrometry in order to evaluate the digestion efficacy by trypsin of proteins contained in a sample. In this context, examples of the sample can specifically include, but not particularly limited to, cell membrane fraction samples obtained by subjecting, for example, cells, tissues, or blood collected from an organism to homogenization treatment using freeze-thawing, French press, glass beads, a homogenizer, an ultrasonic homogenizer, or the like or to fractionation treatment through differential centrifugation, sucrose density gradient centrifugation, or the like. A portion of ntcp protein in the protein for evaluation of the present invention is not particularly limited and can be any DNA encoding an LC/MS/MS-quantifiable amino acid sequence in the ntcp protein. Specific examples thereof can include an amino acid sequence represented by GIYDGDLK (SEQ ID NO: 7).

The peptide fragment for evaluation of the present invention refers to a peptide fragment that is quantified by mass spectrometry in the evaluation protein of the present invention. The peptide fragment for evaluation of the present invention is not particularly limited as long as the peptide fragment has 3 to 20 amino acid residues, has a C-terminal arginine residue (R) or lysine residue (K), has neither arginine nor lysine residues at a site other than the C terminus, differs in amino acid sequence from naturally occurring proteins and their variants, and can be detected by LC/MS/MS. The peptide fragment for evaluation of the present invention is preferably a peptide fragment that has 8, 10, or 12 amino acid residues and contains 1 or 2 proline or glycine residues without histidine. Specific examples thereof can include QIGDPTVPSGVK (SEQ ID NO: 1), NVAPAGPTLK (SEQ ID NO: 2), VGAPGVPALK (SEQ ID NO: 3), and DAPGSGLK (SEQ ID NO: 4). Among them, QIGDPTVPSGVK (SEQ ID NO: 1) can be a preferred example. The peptide fragment for evaluation of the present invention and the peptide fragment for concentration measurement of the present invention differ in use and are therefore defined by different terms. However, these peptide fragments are both included in the substantially the same category.

The evaluation protein of the present invention can be produced, for example, by the following method: a cDNA sequence is designed from the amino acid sequence of the protein for evaluation, and the cDNA is synthesized by, for example, nucleic acid oligo synthesis and PCR. Then, the cDNA is incorporated into an expression vector. The protein is synthesized using *E. coli* or the like. The obtained synthetic protein can be purified under conditions known in the art by a method known in the art such as a purification method using a tag sequence. The accurate amount (concentration) of the purified protein for evaluation can be calculated by amino acid analysis.

Use of the evaluation protein of the present invention enables evaluation of the fragmentation treatment with trypsin of proteins contained in a sample in mass spectrometry. In this context, specific examples of the proteins contained in a sample can include the target protein of the present invention and membrane proteins such as 4F2hc, abcg5, abcg8, oatp1, mct1, bsep, bcrp, ntcp, bgt1, and glut1. The evaluation using the evaluation protein of the present invention can involve, for example: adding a known amount of the protein for evaluation to a sample containing the target protein before fragmentation treatment with trypsin; subjecting the mixture to fragmentation treatment with trypsin; quantifying the obtained peptide fragment for evaluation by LC/MS/MS; and conducting the evaluation on the basis of the obtained quantification value. The peptide fragment for evaluation can be quantified on the basis of a prepared calibration curve. Alternatively, the stable isotope-labeled protein of the present invention may be added, together with the protein for evaluation of the present invention, to the sample containing the target protein before fragmentation treatment with trypsin. The mixture can be subjected to fragmentation treatment with trypsin to prepare stable isotope-labeled target peptide fragments. In this case, the peptide fragment for concentration measurement for the stable isotope-labeled protein of the present invention is preferably selected from peptide fragments differing in amino acid sequence from the peptide fragment for evaluation.

The calibration curve can be prepared by: adding a defined amount of an internal standard stable isotope-labeled peptide fragment for evaluation to peptide fragments for evaluation with several series of known concentrations; subjecting the mixture to mass spectrometry using LC/MS/MS; and calculating the area ratio or peak height ratio between the obtained MS spectra of the peptide fragment for evaluation with each concentration and the stable isotope-labeled peptide fragment for evaluation. Preferably, the amounts of the peptide fragments for evaluation fall within a linear measurement range of the mass spectrometer.

A known amount of an internal standard stable isotope-labeled peptide fragment for evaluation is added to the peptide fragment for evaluation thus obtained by fragmentation treatment with trypsin. The mixture is subjected to mass spectrometry using LC/MS/MS. The area ratio of the mass spectrum of the peptide fragment for evaluation/the mass spectrum of the stable isotope-labeled peptide fragment for evaluation is calculated. The peptide fragment for evaluation can be quantified from the area ratio by calculation using the calibration curve.

The amount (A [mol]) of the protein for evaluation before tryptic digestion treatment and the quantification value (B [mol]) of the peptide fragment for evaluation quantified by mass spectrometry after tryptic digestion treatment can be substituted into the expression (B/[A×The number of the peptide fragments for evaluation contained in the protein for evaluation]) to thereby calculate an evaluation value. When the evaluation value is 0.80 or higher, preferably 0.90 or higher, more preferably 0.95 or higher, the protein can be evaluated as having been sufficiently fragmented with trypsin. An evaluation value (C) derived from a tryptic digestion time that achieves sufficient fragmentation treatment with trypsin and an evaluation value (D) derived from a tryptic digestion time different therefrom can be substituted into the expression (Rate of digestion=D/C) to thereby calculate the rate of digestion. The protein fragmentation treatment with trypsin can also be evaluated on the basis of this rate of digestion. In this context, examples of the tryptic digestion time that achieves sufficient fragmentation treatment with trypsin can include 16 to 36 hours. The tryptic digestion time is preferably 20 to 30 hours, more preferably 24 hours. When the rate of digestion is 0.80 or higher, preferably 0.90 or higher, more preferably 0.95 or higher, the protein can be evaluated as having been sufficiently fragmented with trypsin.

Hereinafter, the present invention will be described more specifically with reference to Examples. However, the technical scope of the present invention is not intended to be limited by these examples.

Example 1

Construction of Protein for Evaluation of the Present Invention

In mass spectrometry, the rate of digestion is calculated using a evaluation protein in order to evaluate the digestion efficacy by trypsin of proteins contained in a sample. Specifically, when the rate of digestion of the protein for evaluation is 100%, the analyte proteins can be evaluated as having been successfully assayed without a loss attributed to undigested proteins in the course of tryptic digestion treatment. In the case of using a conventional evaluation protein, however, analyte proteins having a low rate of tryptic digestion may not be completely digested even at 100% rate of digestion of the protein for evaluation. Thus, an attempt was made to produce a protein for evaluation whose complete digestion could serve as an indicator for evaluating analyte proteins as having been completely digested. For this purpose, membrane proteins generally regarded as having a low rate of digestion were screened for a novel protein for evaluation. Specifically, a mouse liver cell membrane fraction was isolated according to the following method.

The mouse liver was cut into pieces, and an ice-cold hypotonic buffer solution (10 mM NaCl, 1.5 mM $MgCl_2$, 10 mM Tris-HCl, pH 7.4) containing PMSF and a protease inhibitor was added thereto in an amount of 1/100 of the tissue wet weight. The tissue was homogenized using a Teflon® homogenizer (10 strokes) and left standing in ice for 30 minutes. Then, the tissue was homogenized again using a Teflon® homogenizer (20 strokes). The homogenized tissue suspension thus obtained was used as a total tissue lysate. After the tissue homogenization treatment using the Teflon® homogenizer, the homogenization status of the tissue was microscopically confirmed. When the cells were insufficiently homogenized, the homogenized tissue suspension was transferred to a nitrogen gas cell homogenizer. The cells were homogenized by the nitrogen cavitation method (450 psi, 15 min., 4° C.) to prepare the total tissue lysate.

A supernatant was recovered by the centrifugation (10,000 g, 10 min., 4° C.) of the total tissue lysate, and debris fractions were removed therefrom. The resulting supernatant was further ultracentrifuged (100,000 g, 40 min., 4° C.) to recover a pellet. This pellet was suspended in an ice-cold suspension buffer solution [250 mM sucrose (8.56% sucrose), 10 mM Tris-HCl, pH 7.4]. The produced suspension was layered over a 38% sucrose solution (10 mM Tris-HCl, pH 7.4) and ultracentrifuged (100,000 g, 40 min., 4° C.) to recover an intermediate layer. This intermediate layer was ultracentrifuged again (100,000 g, 40 min., 4° C.) The obtained pellet was used as a cell membrane fraction. The recovered cell membrane fraction was suspended in an ice-cold suspension buffer solution [250 mM sucrose (8.56% sucrose), 10 mM Tris-HCl, pH 7.4].

Figure 1:
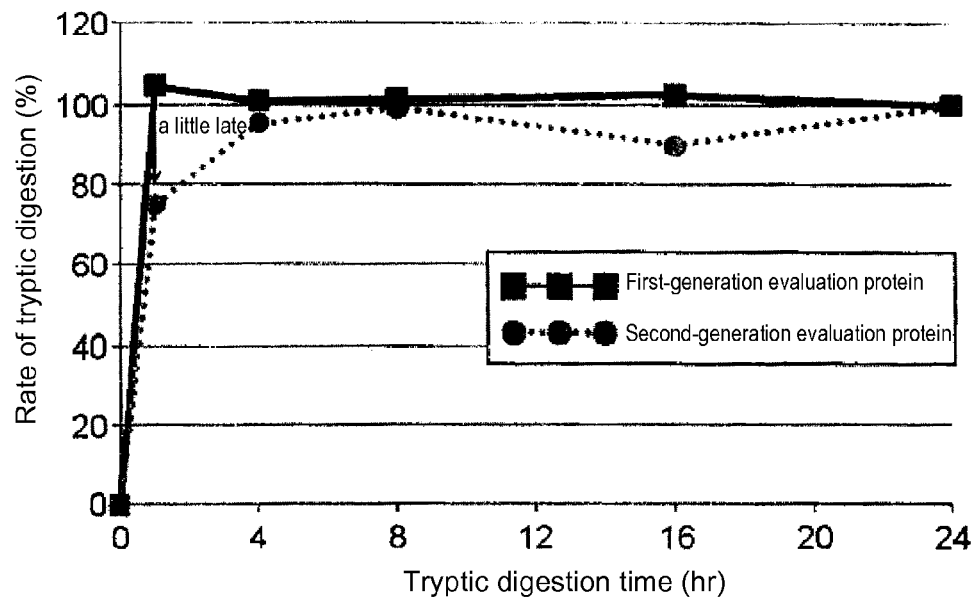
FIG. 1 is a diagram showing time-dependent change in the rates of tryptic digestion of *E. coli* Triose Phosphate Isomerase (TPI) protein (containing a target peptide fragment QIDAVLK [SEQ ID NO: 48]) (first-generation evaluation protein) and a protein consisting of an amino acid sequence represented by SEQ ID NO: 6 (containing target peptide fragments QIGDPTVPSGVK [SEQ ID NO: 1] and NVAPAGPTLK [SEQ ID NO: 2]) (second-generation evaluation protein). The ordinate shows the rate of tryptic digestion (%). The abscissa shows a tryptic digestion time (hr). In the graph, -■- denotes the rate of digestion of the first-generation evaluation protein, and ...●... denotes the rate of digestion of the second-generation evaluation protein. The rate of tryptic digestion is indicated by percentage to an evaluation value derived from a tryptic digestion time of 24 hours as 100.

An 8 M urea solution was added to the cell membrane fraction to denature proteins. Then, incubation (room temperature, 30 min.) treatment in the presence of 250 µg/ml DTT and incubation (room temperature, 60 min.) treatment in the presence of 625 µg/ml iodoacetamide (IAA) were performed in order to protect the SH groups of cysteine residues. Then, 0.1 M Tris-HCl was used to prepare a mixed solution having a final urea concentration of 1.2 M. This mixed solution was equally dispensed to five tubes. After addition of 0.5 µg of trypsin, these tubes were incubated for 1, 4, 8, 16 and 24 hours, respectively, in a thermostat bath of 37° C. The peptide fragments thus obtained by tryptic digestion were quantified using a mass spectrometer (API5000). The controls used were in vitro expressed E. coli Triose Phosphate Isomerase (TPI) protein (containing a target peptide fragment QIDAVLK [SEQ ID NO: 48]) (first-generation evaluation protein) and a protein consisting of the amino acid sequence represented by SEQ ID NO: 6 (containing peptide fragments for evaluation; QIGDPTVPSGVK [SEQ ID NO: 1] and NVAPAGPTLK [SEQ ID NO: 2]) (second-generation evaluation protein). As shown in FIG. 1, the second-generation evaluation protein has a lower rate of digestion than that of the first-generation evaluation protein.

Figure 2:
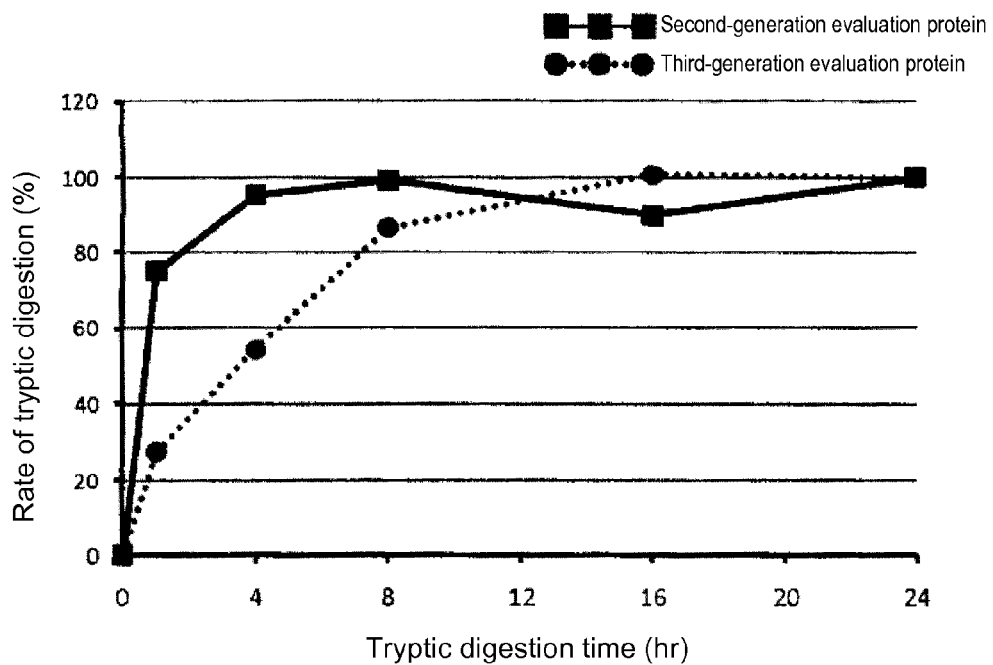
FIG. 2 is a diagram showing time-dependent change in the rates of tryptic digestion of the second-generation evaluation protein and a protein in which GIYDGDLK (SEQ ID NO: 7) in ntcp protein (SEQ ID NO: 8) was substituted by QIGDPTVPSGVK (SEQ ID NO: 1) (third-generation evaluation protein: SEQ ID NO: 5). The ordinate shows the rate of tryptic digestion (%). The abscissa shows a tryptic digestion time (hr). In the graph, -■- denotes the rate of digestion of the second-generation evaluation protein, and ...●... denotes the rate of digestion of the third-generation evaluation protein. The rate of tryptic digestion is indicated by percentage to an evaluation value derived from a tryptic digestion time of 24 hours as 100.
Figure 3:
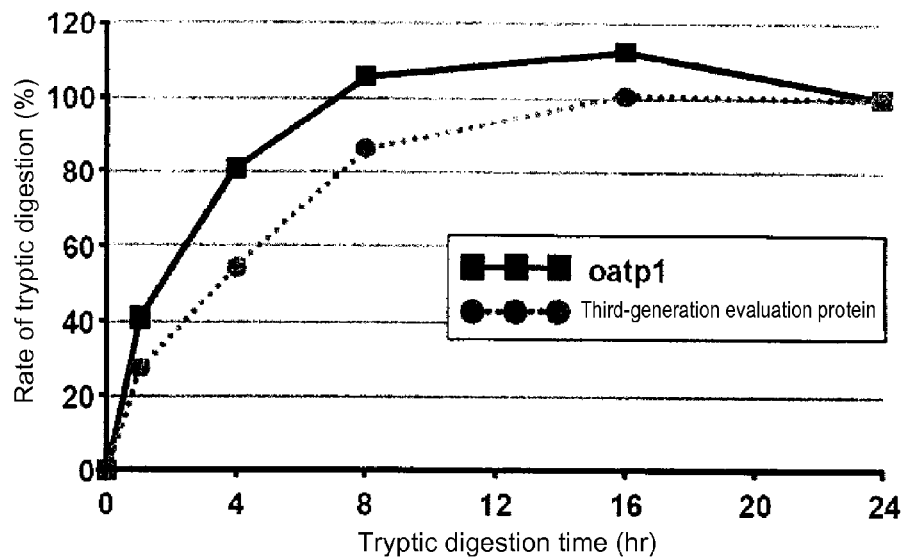
FIG. 3 is a diagram showing time-dependent change in the rates of tryptic digestion of Organic Anion Transporting Polypeptide 1 (oatp1) protein and the third-generation evaluation protein. The ordinate shows the rate of tryptic digestion (%). The abscissa shows a tryptic digestion time (hr). In the graph, -■- denotes the rate of digestion of the oatp1 protein, and ...●... denotes the rate of digestion of the third-generation evaluation protein. The rate of tryptic digestion is indicated by percentage to an evaluation value derived from a tryptic digestion time of 24 hours as 100.
Figure 4:
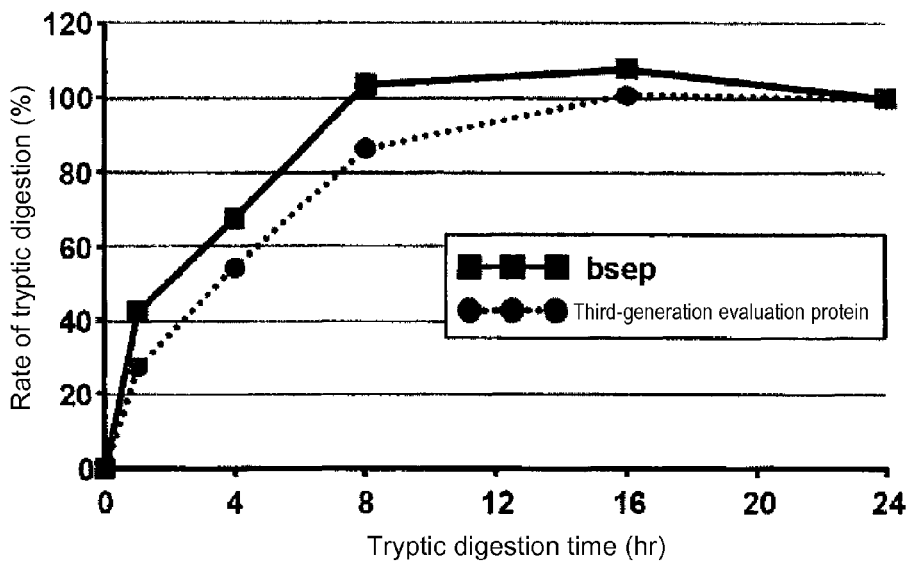
FIG. 4 is a diagram showing time-dependent change in the rates of tryptic digestion of Bile salt export pump (bsep) protein and the third-generation evaluation protein. The ordinate shows the rate of tryptic digestion (%). The abscissa shows a tryptic digestion time (hr). In the graph, -■- denotes the rate of digestion of the bsep protein, and ... ●... denotes the rate of digestion of the third-generation evaluation protein. The rate of tryptic digestion is indicated by percentage to an evaluation value derived from a tryptic digestion time of 24 hours as 100.
Figure 5:
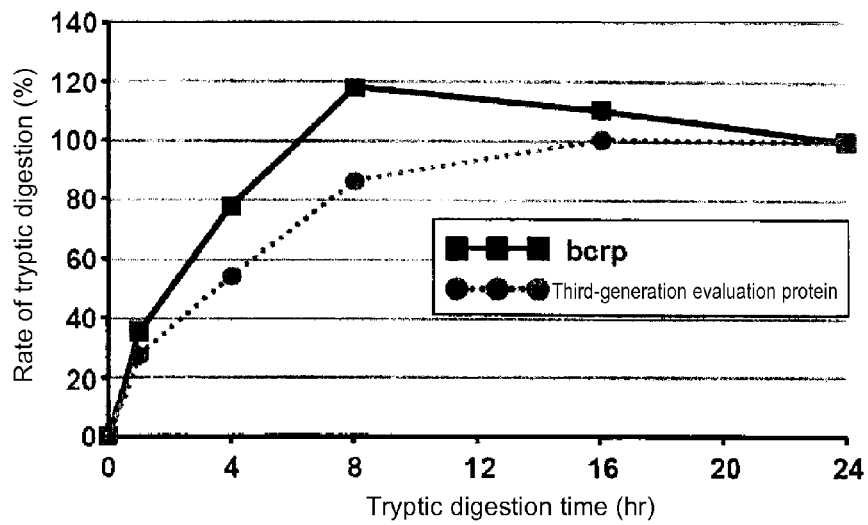
FIG. 5 is a diagram showing time-dependent change in the rates of tryptic digestion of Breast cancer resistance protein (bcrp) protein and the third-generation evaluation protein. The ordinate shows the rate of tryptic digestion (%). The abscissa shows a tryptic digestion time (hr). In the graph, -■- denotes the rate of digestion of the bcrp protein, and ... ●... denotes the rate of digestion of the third-generation evaluation protein. The rate of tryptic digestion is indicated by percentage to an evaluation value derived from a tryptic digestion time of 24 hours as 100.
Figure 6:
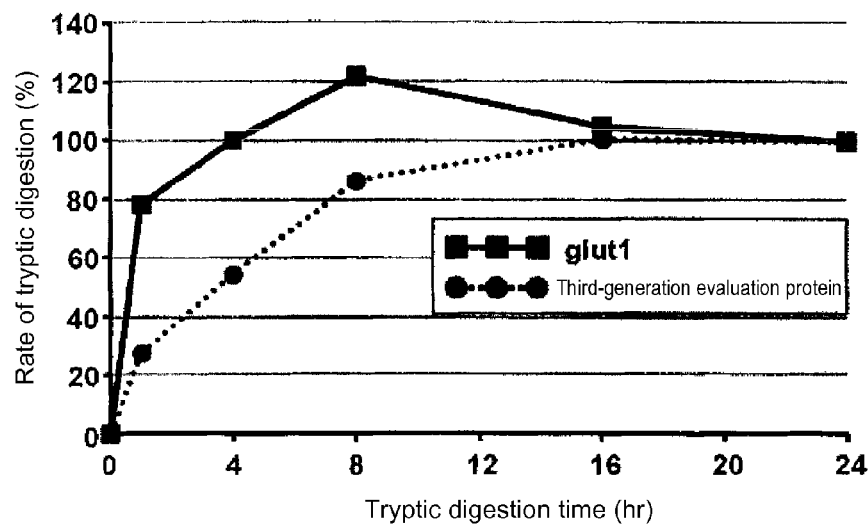
FIG. 6 is a diagram showing time-dependent change in the rates of tryptic digestion of Glucose transporter 1 (glut1) protein and the third-generation evaluation protein. The ordinate shows the rate of tryptic digestion (%). The abscissa shows a tryptic digestion time (hr). In the graph, -■- denotes the rate of digestion of the glut1 protein, and ... ●... denotes the rate of digestion of the third-generation evaluation protein. The rate of tryptic digestion is indicated by percentage to an evaluation value derived from a tryptic digestion time of 24 hours as 100.

The rate of tryptic digestion was determined as to 12 types of membrane proteins (4F2hc, mrp6, abcg5, abcg8, oatp1, oatp2, mct1, bsep, bcrp, ntcp, bgt1, and Na/K ATPase). As a result, 4 types of membrane proteins (4F2hc, oatp1, bsep, and Na/K ATPase) had a higher rate of digestion than that of the second-generation evaluation protein. By contrast, 8 types of proteins (mrp6, abcg5, abcg8, oatp2, mct1, bcrp, ntcp, and bgt1) were shown to have a lower rate of digestion than that of the second-generation evaluation protein. Among them, the ntcp protein was shown to have the lowest rate of tryptic digestion. Thus, a peptide fragment produced by the tryptic treatment of the ntcp protein (SEQ ID NO: 8), i.e., an LC/MS/MS target peptide fragment GIYDGDLK (SEQ ID NO: 7), was substituted by a peptide fragment for evaluation consisting of the amino acid sequence represented by QIGDPTVPSGVK (SEQ ID NO: 1) to construct a protein (third-generation evaluation protein: SEQ ID NO: 5). Results of verifying the rate of digestion of this third-generation evaluation protein demonstrated that the third-generation evaluation protein further had a lower rate of digestion than that of the second-generation evaluation protein (FIG. 2). As a result of comparing the rate of digestion between the third-generation evaluation protein and 10 types of membrane proteins (4F2hc, abcg5, abcg8, oatp1, mct1, bsep, bcrp, ntcp, bgt1, and glut1), the third-generation evaluation protein was shown to have a lower rate of digestion compared with 7 types of proteins (4F2hc, abcg5, abcg8, oatp1, bsep, bcrp, and glut1) except for mct1, ntcp, and bgt1 (FIGS. 3 to 6). These results show that the second-generation evaluation protein has a lower rate of digestion compared with 4 types of membrane proteins among 12 types of membrane proteins, whereas the third-generation evaluation protein has a lower rate of digestion compared with 7 types of membrane proteins among 10 types of membrane proteins. These results demonstrated that the third-generation evaluation protein enables evaluation of the digestion treatment of more target proteins than those by the second-generation evaluation protein.

Example 2

Improvement in Fragmentation Treatment with Trypsin of the Present Invention

Figure 7:
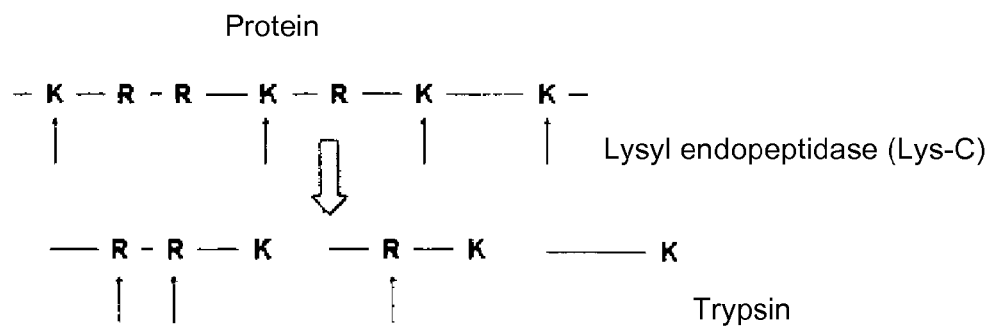
FIG. 7 is a diagram summarizing an enzymatic protein treatment step in the method (1) for quantifying a membrane protein according to the present invention. In the diagram, K represents a lysine residue, and R represents an arginine residue.

The present inventors considered improving the digestion method in order to enhance the rate of tryptic digestion of membrane proteins, which are indigestible proteins. Trypsin is an enzyme that hydrolyzes the carboxyl-terminal peptide bonds of lysine (K) and arginine (R). This enzyme has been thought to have lower cleavage efficiency for the lysine residue than that for the arginine residue. Thus, in this experiment, trypsin was studied for whether its combined use with lysyl endopeptidase (hereinafter, also referred to as "Lys-C"), an enzyme having the activity of cleaving lysine residues, allowed for efficient protein degradation (FIG. 7).

The cell membrane fraction prepared in Example 1 was digested with trypsin alone, and its rate of digestion was compared with the rate of digestion of the cell membrane fraction by 3-hour digestion with Lys-C followed by 16-hour tryptic digestion. The reaction conditions of trypsin and Lys-C are as follows.

<Trypsin>
Trypsin: Sequencing Grade Modified Trypsin, Frozen (manufactured by Promega Corp.)
Concentration: 1/100 of protein level
Buffer composition: 1.2 M urea, 0.1 M Tris-HCl, 0.05% Protease Max™ Surfactant
Temperature: 37° C.

<Lys-C>
Lys-C: Lysyl Endopeptidase for Biochemistry (manufactured by Wako Pure Chemical Industries, Ltd.)
Concentration: 1/100 of protein level
Buffer composition: 1.2 M urea, 0.1 M Tris-HCl, 0.05% Protease Max™ Surfactant
Temperature: room temperature (15 to 25° C.)

Figure 8:
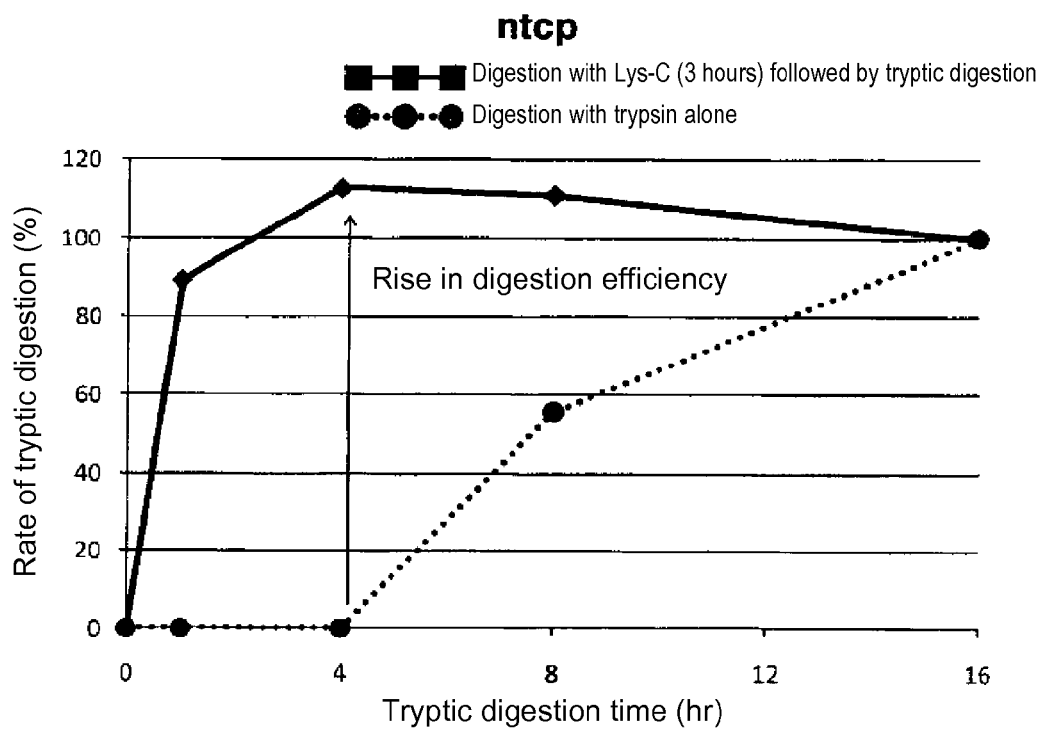
FIG. 8 is a diagram showing time-dependent change in the rates of digestion of ntcp protein by digestion with trypsin alone and by digestion using lysine endopeptidase (Lys-C) and trypsin in combination. The ordinate shows the rate of tryptic digestion (%). The abscissa shows a tryptic digestion time (hr). In the graph, -♦- denotes the rate of digestion by 3-hour digestion with Lys-C followed by tryptic digestion, and ... ●... denotes the rate of digestion by digestion with trypsin alone. The rate of tryptic digestion is indicated by percentage to a quantification value derived from a tryptic digestion time of 16 hours as 100.
Figure 9:
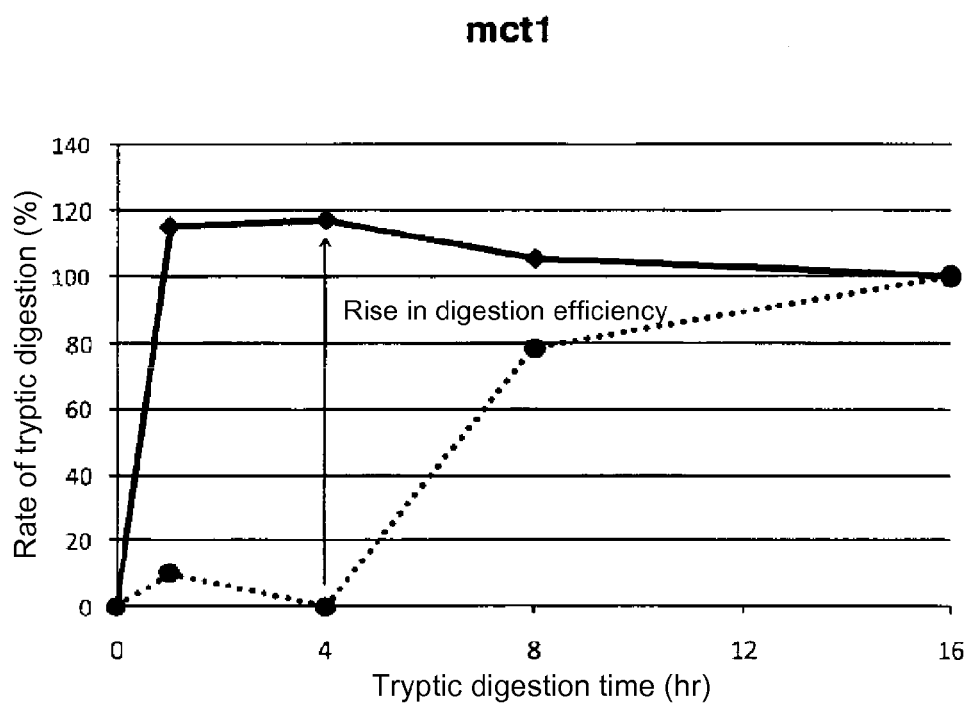
FIG. 9 is a diagram showing time-dependent change in the rates of digestion of Monocarboxylate transporter 1 (mct1) protein by digestion with trypsin alone and by digestion using lysine endopeptidase (Lys-C) and trypsin in combination. The ordinate shows the rate of tryptic digestion (%). The abscissa shows a tryptic digestion time (hr). In the graph, -♦- denotes the rate of digestion by 3-hour digestion with Lys-C followed by tryptic digestion, and ... ●... denotes the rate of digestion by digestion with trypsin alone. The rate of tryptic digestion is indicated by percentage to a quantification value derived from a tryptic digestion time of 16 hours as 100.

The results are shown in FIGS. 8 and 9. As is evident from FIGS. 8 and 9, the digestion with Lys-C followed by tryptic digestion, compared with the digestion with trypsin alone, showed a substantial rise in the rates of digestion of both ntcp protein and mct1 protein. Next, study was made on the difference in the LC/MS/MS quantification values of 4F2hc, mrp6, abcg5, abcg8, oatp1, mct1, bsep, ntcp, glut1, bgt1, and Na/K ATPase between 16-hour digestion with trypsin alone and 3-hour digestion with Lys-C followed by tryptic digestion. As seen from the results shown in FIG. 10, ntcp exhibited a quantification value of 3.72 in the case of digestion with trypsin alone, but exhibited a quantification value of 26.2 in the case of digestion with Lys-C followed by tryptic digestion, indicating a difference as large as 7 times. These results demonstrated that digestion with Lys-C followed by tryptic digestion enables efficient fragmentation treatment and can yield a more accurate quantification value.

Example 3

Figure 11:
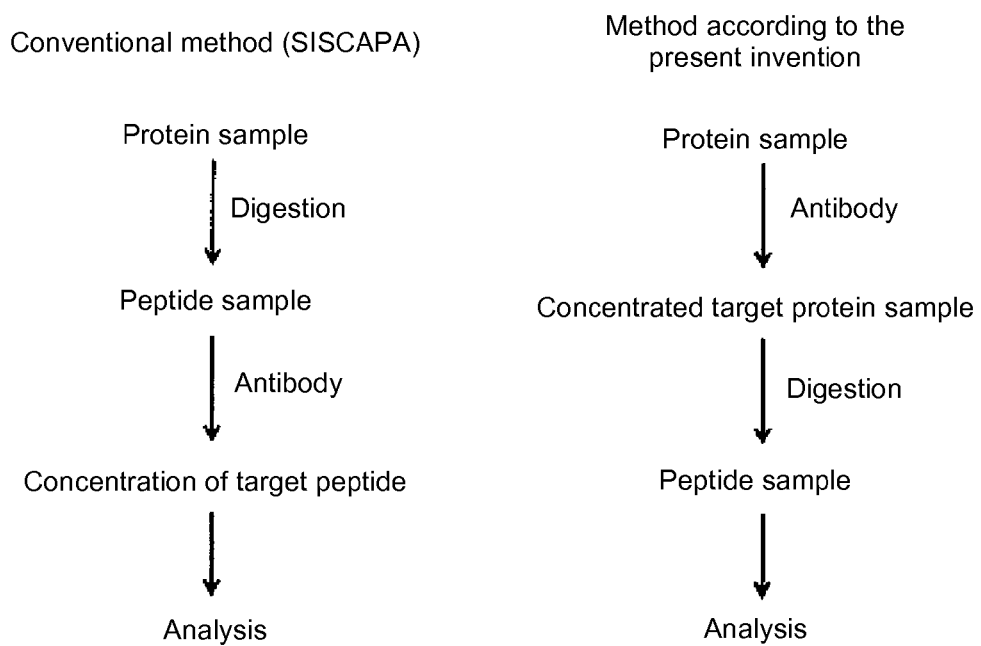
FIG. 11 is a diagram showing the comparison between a conventional method (SISCAPA) and the method according to the present invention as methods for concentrating peptide fragments using antibodies.

Improvement in Method for Preparing Sample Containing Target Protein of the Present Invention Since the cell membrane fraction contained large amounts of impurities, this seemed to be responsible for reduction in the rate of tryptic digestion. SISCAPA is known as a method for removing impurities. The SISCAPA method involves subjecting a protein sample to digestion treatment and concentrating the resulting peptide fragments by affinity purification using antibodies that recognize the peptide fragments (FIG. 11, left). The SISCAPA method can reduce impurities contained in the protein sample prior to mass spectrometry and can therefore increase the peak intensity of the peptide fragments to be detected. This method, however, requires antibodies against the target peptide fragments in each case and is therefore disadvantageous in terms of convenience. The present inventors considered that if target peptide fragments could be concentrated using antibodies recognizing proteins, a wide range of antibodies could be used without being limited by antibodies recognizing the target peptide fragments. Thus, study was made on a method using antibodies recognizing proteins to affinity-purify a protein sample before digestion treatment (FIG. 11, right).

A human lung cancer cell line (H1975) was recovered and then suspended in an ice-cold hypotonic buffer solution (137 mM NaCl, 8.10 mM $Na_2HPO_4.12H_2O$, 2.68 mM KCl, 1.47 mM $KH_2PO_4$) containing PMSF and a protease inhibitor in an amount of 1/100 of the tissue wet weight. Then, a cell membrane fraction was prepared according to the method of Example 1. This cell membrane fraction was affinity-purified using anti-EGFR antibodies. Hereinafter, a detailed method will be described. The cell membrane fraction thus prepared was added to an anti-EGFR antibody-immobilized microwell strip plate of a kit (PathScan® Total EGFReceptor Sandwich ELISA Kit #7250 [manufactured by Cell Signaling Technology, Inc.]). The plate was incubated at 37° C. for 2 hours. Then, the solution in each well was discarded, and the well was washed, followed by affinity purification.

Figure 12:
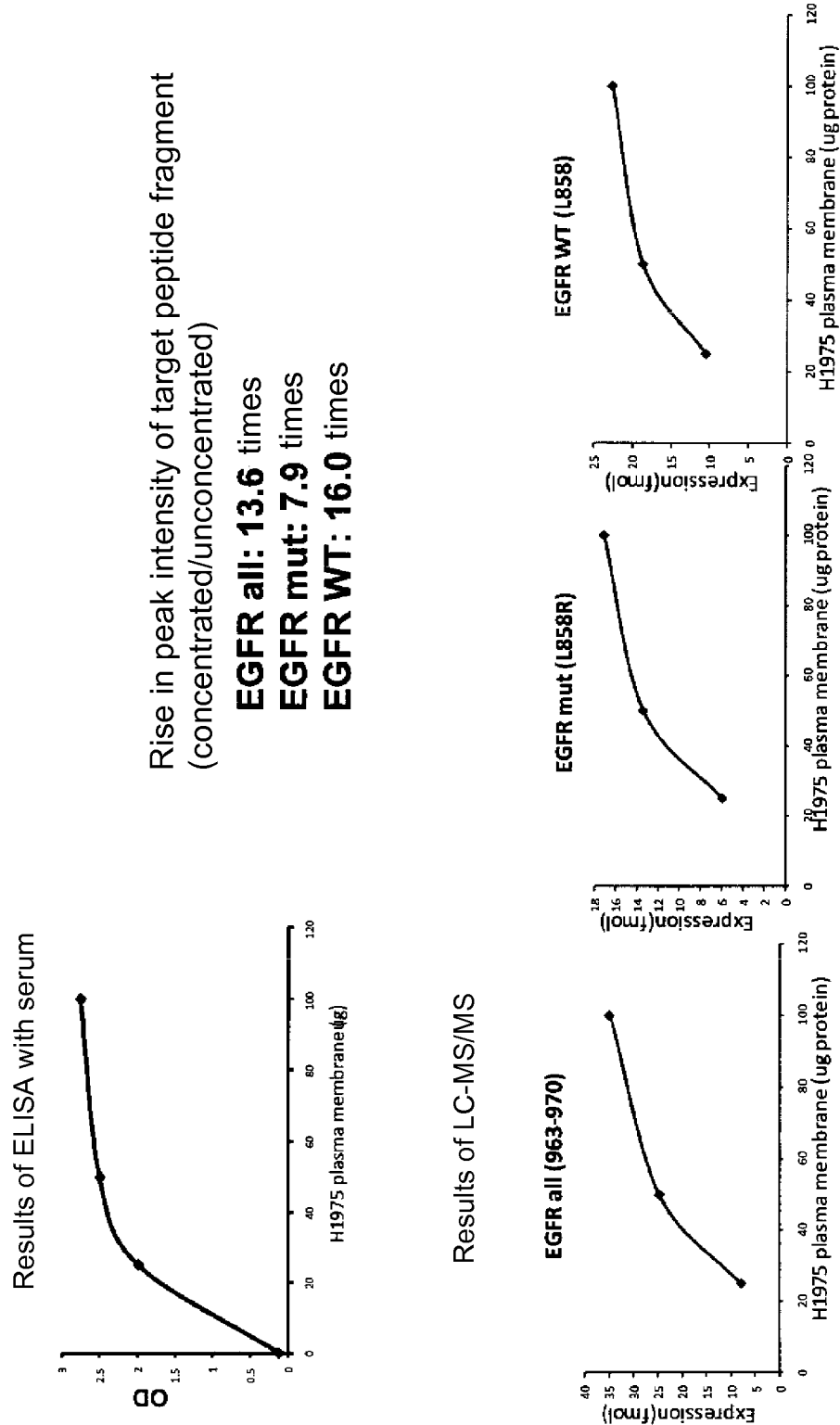
FIG. 12 is a diagram showing results of quantifying, by ELISA (upper graph) and LC/MS/MS (lower graphs), the expression levels of EGFR (EGFR all[963-970]) and two EGFR variants (EGFR mut[L858R] and EGFR WT[L858]) contained in the cell membrane fraction of a human lung cancer cell line (H1975).

After the concentration of EGFR protein by affinity purification, a peptide fragment sample was obtained by the tryptic digestion treatment of Example 2. ELIIEFSK (SEQ ID NO: 9) (EGFR all[963-970]) of EGFR and ITDFGR (SEQ ID NO: 10) (EGFR mut[L858R]) and ITDFGLAK (SEQ ID NO: 11) (EGFR WT[L858]) respectively contained in two EGFR variants were selected as target peptide fragments. These types of target peptide fragments were quantified by LC/MS/MS (FIG. 12). Results of comparing the concentrated EGFR protein sample with an unconcentrated EGFR protein sample demonstrated that the concentration of the EGFR protein increased the peak intensity of EGFR all (963-970), EGFR mut(L858R), and EGFR WT(L858) by 13.6 times, 7.9 times, and 16.0 times, respectively. In addition, the sample containing the peptide fragments was mixed with serum (human serum, fro, human male AB plasma, sterile-filtered H4522 [manufactured by Sigma-Aldrich Corp.]). This mixed solution was analyzed by ELISA. The obtained results were shown to be consistent with the results of LC/MS/MS (FIG. 12). These results suggest that the concentration of the EGFR protein can remove foreign proteins and consequently reduce ion suppression to thereby increase peak intensity.

Example 4

Preparation of Stable Isotope-Labeled Protein of the Present Invention

Figure 13:
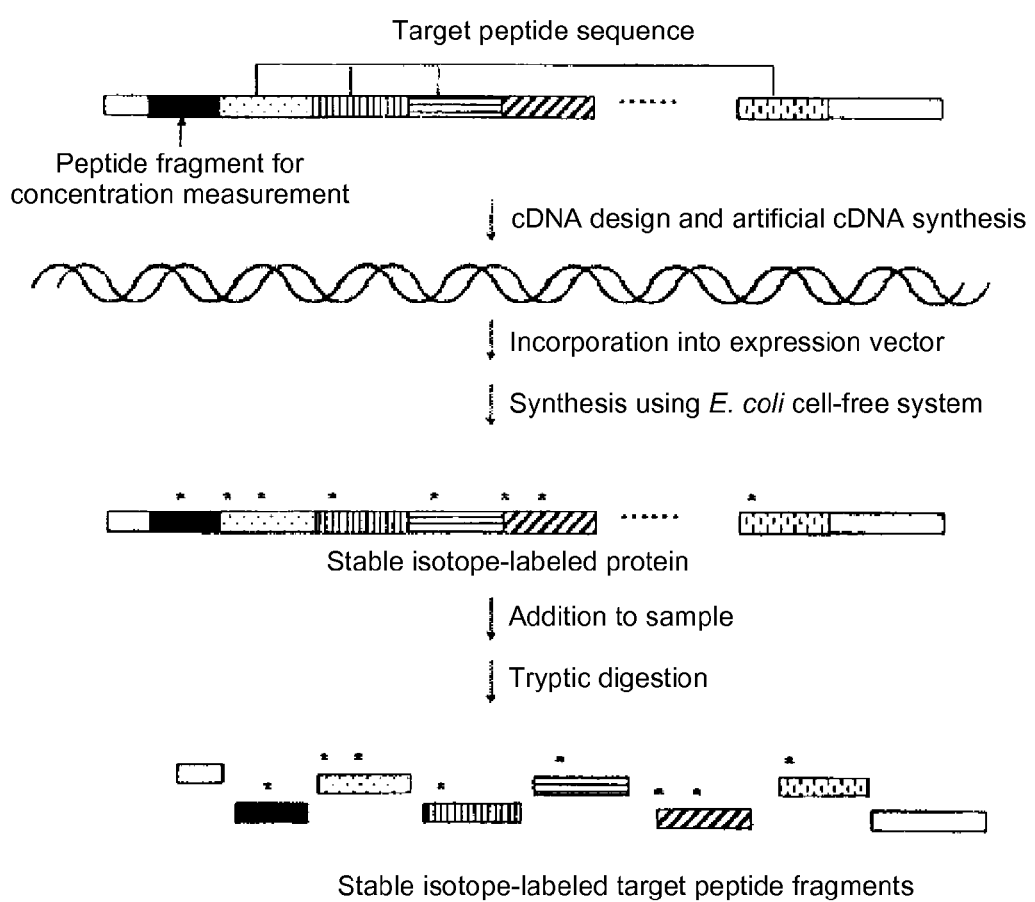
FIG. 13 is a diagram summarizing the stable isotope-labeled protein of the present invention and the method for producing a stable isotope-labeled peptide fragment according to the present invention.

The comprehensive quantitative analysis of target proteins by mass spectrometry requires the number of stable isotope-labeled target peptide fragments for use as internal standards according to the number of target peptide fragments to be quantified. The stable isotope-labeled target peptide fragments are generally outsourced. This costs around 100,000 yen per type and therefore presents cost problems. Thus, study was made on a method for producing a stable isotope-labeled target peptide fragment more inexpensively and conveniently. The stable isotope-labeled target peptide fragments were prepared according to a method shown below. This method is summarized in FIG. 13.

A DNA encoding a peptide fragment for concentration measurement (QIGDPTVPSGVK: SEQ ID NO: 1) was conjugated with the 5' end of a tandemly linked DNA in which DNAs encoding 36 types of target peptide fragments for detection of general diagnostic markers were linked in tandem, to synthesize a DNA conjugate. This DNA conjugate was inserted to a pET-vector. A stable isotope-labeled protein was expressed by incubation at 30° C. for 16 hours in a reaction solution containing an *E. coli* extract (Musaibo-kun Quick [manufactured by Taiyo Nippon Sanso Corp.]), ATP as energy, and stable isotope-labeled lysine and arginine. The reaction solution containing the stable isotope-labeled protein was subjected to solubilization treatment in the presence of 8 M urea. Then, an aliquot thereof was fractionated by SDS-PAGE. Then, the expression of the stable isotope-labeled protein was confirmed by detection using CBB R-250. The solution after the solubilization treatment was adjusted to a final urea concentration of 1.2 M with 0.5 M Tris-HCl (pH 8.5). Then, trypsin was added thereto in an amount of 1/100 of the protein level, and the mixture was incubated at 37° C. for 16 hours to prepare stable isotope-labeled target peptide fragments. Since the absolute amount of the peptide fragment for concentration measurement is equal to the absolute amount of the stable isotope-labeled protein, the concentration of the peptide fragment for concentration measurement was measured by an absolute quantification method based on LC-MS/MS to calculate the concentration of the stable isotope-labeled protein.

Detection Sensitivity for Stable Isotope-Labeled Target Peptide Fragment

The soluble fraction containing 2020 fmol of the stable isotope-labeled protein was subjected to the tryptic digestion treatment of Example 2. Then, detection sensitivity for stable isotope-labeled peptide fragments was determined by LC/MS/MS. The results are shown in FIG. 14. The obtained peak areas (counts) of 36 types of peptide fragments were multiplied by "10 fmol/2020 fmol". As a result, all the peptide fragments exhibited detectable 1000 counts or higher, demonstrating that the sensitivity can achieve sufficient detection of 10 fmol of the peptide fragment.

Hereinafter, these 36 types of peptide fragments obtained by digestion treatment will be shown.

SSDYFGNGR (SEQ ID NO: 12): serum amylase

IYVSDDGK (SEQ ID NO: 13): serum amylase

QGLLPVLESFK (SEQ ID NO: 14): Apo-A1

DLATVYVDVLK (SEQ ID NO: 15): Apo-A1

SPELQAEAK (SEQ ID NO: 16): Apo-A2

IEIPLPFGGK (SEQ ID NO: 17): Apo-B(48 + 100)

EFQVPTFTIPK (SEQ ID NO: 18): Apo-B(48 + 100)

NPNGYSFSIPVK (SEQ ID NO: 19): Apo-B100

NIILPVYDK (SEQ ID NO: 20): Apo-B100

TYLPAVDEK (SEQ ID NO: 21): Apo-C2

GWVTDGFSSLK (SEQ ID NO: 22): Apo-C3

LGPLVEQGR (SEQ ID NO: 23): Apo-E

ITWSNPPAQGAR (SEQ ID NO: 24): GOT, cytoplasmic

LALGDDSPALK (SEQ ID NO: 25): GOT, cytoplasmic

FVTVQTISGTGALR (SEQ ID NO: 26): GOT, mitochondrial

ILVSGGGK (SEQ ID NO: 27): GPT

TPSSWGR (SEQ ID NO: 28): GPT

LVIITAGAR (SEQ ID NO: 29): LDH M subunit

-continued

IVVVTAGVR (SEQ ID NO: 30): LDH H subunit

FPFVALSK (SEQ ID NO: 31): ALP

LFQPSIQLAR (SEQ ID NO: 32): γ-GTP

GGLSVAVPGEIR (SEQ ID NO: 33): γ-GTP

EPQVYTLPPSR (SEQ ID NO: 34): ZTT

ALPAPIEK (SEQ ID NO: 35): ZTT

NIAAFGGNPK (SEQ ID NO: 36): CHE

FWTSFFPK (SEQ ID NO: 37): CHE

INGIPQQHTQVLFIAK (SEQ ID NO: 38): CEA

HSQPWQVLVASR (SEQ ID NO: 39): PSA

LTSPVVTTSTR (SEQ ID NO: 40): CA125

FPDIFSVASSR (SEQ ID NO: 41): CA125

SSVPSSTEK (SEQ ID NO: 42): CA15-3

ATTTPASK (SEQ ID NO: 43): CA15-3

ILGATIENSR (SEQ ID NO: 44): CYFRA

ANTFLEEVR (SEQ ID NO: 45): PIVKA-II

VLQGLPR (SEQ ID NO: 46): HER2

GGVLIQR (SEQ ID NO: 47): HER2

Example 5

Method for Evaluating Synthesis of Full-Length Stable Isotope-Labeled Protein of the Present Invention The concentrations of the stable isotope-labeled protein produced by the method described in Example 4 and each stable isotope-labeled target peptide fragment constituting this protein are determined from the concentration of the peptide fragment for concentration measurement. This is based on the premise that the stable isotope-labeled protein is completely synthesized. In some cases, the stable isotope-labeled protein may not be completely synthesized for some reason. Thus, study was made on a method for detecting such cases. Specifically, a peptide fragment for concentration measurement was added to the amino terminus of the stable isotope-labeled protein, while another peptide fragment for concentration measurement was added to the carboxyl terminus thereof. The concentrations of both the terminal peptide fragments for concentration measurement were measured and compared. This method was studied for its ability to evaluate whether the stable isotope-labeled protein was completely synthesized (FIG. 15). First, MP1 (SEQ ID NO: 49) and MP2 (SEQ ID NO: 50) were designed as model proteins for verifying whether the full-length stable isotope-labeled protein was synthesized. MP1 had: a peptide fragment for concentration measurement (QIGDPTVPSGVK: SEQ ID NO: 1) (hereinafter, referred to as a "peptide fragment A for concentration measurement") added to the amino terminus of a tandemly linked protein (SEQ ID NO: 51) in which target peptide fragments were linked in tandem; and another peptide fragment for concentration measurement (NVAPAGPTLK: SEQ ID NO: 2) (hereinafter, referred to as a "peptide fragment B for concentration measurement") added to the carboxyl terminus of this tandemly linked protein. MP2 had: the peptide fragment A for concentration measurement added to the amino terminus of a tandemly linked protein (SEQ ID NO: 52) in which target peptide fragments were linked in tandem; and the peptide fragment B for concentration measurement added to the carboxyl terminus of this tandemly linked protein. Subsequently, in order to express these 2 types of proteins (MP1 and MP2), a DNA encoding the peptide fragment A for concentration measurement was conjugated with the 5' end of a tandemly linked DNA encoding each tandemly linked protein, while a DNA encoding the peptide fragment B for concentration measurement was conjugated with the 3' end of the tandemly linked DNA to synthesize a DNA conjugate. The synthesized DNA conjugate was inserted to a pET-vector. The proteins were synthesized by incubation at 30° C. for 16 hours in a reaction solution containing an *E. coli* extract (Musaibo-kun Quick [manufactured by Taiyo Nippon Sanso Corp.]) and ATP as energy. This analysis was conducted by focusing attention on evaluating whether the stable isotope-labeled model proteins were completely synthesized. Accordingly, the protein synthesis was carried out in the absence of stable isotope-labeled amino acids.

The synthesized 2 types of proteins (MP1 and MP2) were each subjected to solubilization treatment in the presence of 8 M urea. Then, each solution was adjusted to a final urea concentration of 1.2 M with 0.5 M Tris-HCl (pH 8.5). Then, trypsin was added thereto in an amount of 1/100 of the protein level, and the mixture was incubated at 37° C. for 16 hours to prepare target peptide fragments and peptide fragments A and B for concentration measurement. Stable isotope-labeled peptide fragments A and B for concentration measurement with a known concentration (500 fmol) were used as internal standards to quantify the concentrations of the peptide fragments A and B for concentration measurement by LC/MS/MS. The obtained quantification values (Table 1 and FIG. 16) of the peptide fragments A and B for concentration measurement were substituted into the expression (Quantification value of the peptide fragment B for concentration measurement/Quantification value of the peptide fragment A for concentration measurement) to calculate the ratios of the completely synthesized model proteins ("Ratio of full length" in FIG. 15 and Table 1). The results are shown in Table 1. The "ratio of full length" was 0.87 in the case of using the model protein MP2. This means that 87% of the synthesized MP2 proteins can be evaluated as having the full length. On the other hand, the "ratio of full length" was 0.23 in the case of using the model protein MP1. This means that 23% of the synthesized MP1 proteins can be evaluated as having the full length.

hese results demonstrated that the peptide fragments for concentration measurement are added to the amino terminus and carboxyl terminus, respectively, of the stable isotope-labeled protein, and the concentrations of both the terminal peptide fragments for concentration measurement can be measured to thereby evaluate the complete protein synthesis of the stable isotope-labeled protein. For example, when the majority of the synthesized stable isotope-labeled proteins have a full length as shown in the results about MP2, the stable isotope-labeled protein can be prepared without a purification step of the full-length stable isotope-labeled proteins. Alternatively, when only a small proportion of the synthesized stable isotope-labeled proteins have a full length as shown in the results about MP1, measures such as study on protein synthesis conditions or addition of tags (e.g., HAT tag) to the carboxyl terminus to purify the full-length stable isotope-labeled proteins can be taken to prepare the stable isotope-labeled protein.

TABLE 1

| Protein | Peptide fragment A for concentration measurement pmol/50 μL | | Peptide fragment B for concentration measurement pmol/50 μL | | Ratio of full length % | Molecular weight of protein kDa |
|---|---|---|---|---|---|---|
| | Mean | SEM | Mean | SEM | | |
| MP1 | 8.4 | 0.4 | 1.9 | 0.2 | 23 | 47 |
| MP2 | 25.8 | 0.9 | 22.5 | 0.6 | 87 | 51 |

The quantification values of the peptide fragments A and B for concentration measurement are indicated by mean±standard deviation (SEM) (n=4).

---

The invention claimed is:

1. A method for producing a stable isotope-labeled target peptide fragment in mass spectrometry, comprising the following steps (a) to (d):
   (a) expressing a DNA conjugate in a system having a stable isotope-labeled amino acid to thereby prepare a stable isotope-labeled protein, wherein the DNA conjugate comprises:
   a tandemly linked DNA in which two or more DNAs encoding one or more types of target peptide fragments are linked in tandem;
   a DNA encoding a peptide fragment for concentration measurement conjugated with the 5' end of the tandemly linked DNA; and
   a DNA encoding a peptide fragment for concentration measurement conjugated with the 3' end of the tandemly linked DNA differing in amino acid sequence from the peptide fragment for concentration measurement encoded by the DNA conjugated with the 5' end of the tandemly linked DNA; and
   wherein the peptide fragments for concentration measurement are different in amino acid sequence from naturally occurring proteins and their variants, and detectable by a liquid chromatograph-tandem mass spectrometer (LC/MS/MS);
   (b) subjecting the stable isotope-labeled protein to digestion by trypsin to prepare stable isotope-labeled peptide fragments for concentration measurement and stable isotope-labeled target peptide fragments;
   (c) quantifying the stable isotope-labeled peptide fragments for concentration measurement using LC/MS/MS; and
   (d) calculating the concentration of the stable isotope-labeled target peptide fragments from the quantification value of the stable isotope-labeled peptide fragments for concentration measurement.

2. The production method according to claim 1, wherein the fragmentation treatment with trypsin is digestion using trypsin and lysyl endopeptidase in combination.

3. The production method according to claim 1, wherein the peptide fragments for concentration measurement consist of an amino acid sequence represented by QIGDPTVPSGVK (SEQ ID NO: 1) or NVAPAGPTLK (SEQ ID NO: 2).

4. The production method according to claim 1, wherein the stable isotope-labeled protein is obtained by the expression of a DNA in which a portion of a DNA encoding ntcp protein consisting of the amino acid sequence represented by SEQ ID NO: 8 is substituted by the DNA conjugate.

5. A method for quantifying a target protein in a sample, comprising the following steps (A) to (G):
   (A) expressing a DNA conjugate in a system having a stable isotope-labeled amino acid to thereby prepare a stable isotope-labeled protein, wherein the DNA conjugate comprises:
   a tandemly linked DNA in which two or more DNAs encoding one or more types of target peptide fragments contained in target protein(s) are linked in tandem;
   a DNA encoding a peptide fragment for concentration measurement conjugated with the 5' end of the tandemly linked DNA; and
   a DNA encoding a peptide fragment for concentration measurement conjugated with the 3' end of the tandemly linked DNA differing in amino acid sequence from the peptide fragment for concentration measurement encoded by the DNA conjugated with the 5' end of the tandemly linked DNA; and
   wherein the peptide fragments for concentration measurement are different in amino acid sequence from naturally occurring proteins and their variants, and detectable by a liquid chromatograph-tandem mass spectrometer (LC/MS/MS);
   (B) subjecting the stable isotope-labeled protein to digestion by trypsin to prepare a stable isotope-labeled peptide fragment for concentration measurement and stable isotope-labeled target peptide fragments;
   (C) quantifying the stable isotope-labeled peptide fragments for concentration measurement using LC/MS/MS;
   (D) calculating the concentration of the stable isotope-labeled target peptide fragments from the quantification value of the stable isotope-labeled peptide fragments for concentration measurement;
   (E) subjecting a sample comprising one or more types of target proteins to digestion by trypsin to prepare target peptide fragments;
   (F) using, as internal standards, the stable isotope-labeled target peptide fragments with the known concentration obtained by the steps (A) to (D) to quantify the target peptide fragments obtained in the step (E) using a liquid chromatograph-tandem mass spectrometer (LC/MS/MS); and
   (G) calculating the concentration of the target protein from the quantification value of the target peptide fragments.

6. The quantification method according to claim 5, further comprising a step (p) of, before the digestion by trypsin, contacting the target proteins with antibodies capable of specifically binding to the target proteins to purify the target proteins in advance.

7. The quantification method according to claim 5, wherein the digestion by trypsin is digestion using trypsin and lysyl endopeptidase in combination.

8. The quantification method according to claim 5, wherein the peptide fragments for concentration measurement consist of the amino acid sequence represented by QIGDPTVPSGVK (SEQ ID NO: 1) or NVAPAGPTLK (SEQ ID NO: 2).

9. The quantification method according to claim 5, wherein the stable isotope-labeled protein is obtained by the expression of a DNA in which a portion of a DNA encoding ntcp protein consisting of the amino acid sequence represented by SEQ ID NO: 8 is substituted by the DNA conjugate.

10. A method for quantifying a target protein in a sample, comprising the following steps (A') to (G'):
   (A') expressing a DNA conjugate in a system having a stable isotope-labeled amino acid to thereby prepare a stable isotope-labeled protein, wherein the DNA conjugate comprises:
      a tandemly linked DNA in which two or more DNAs encoding one or more types of target peptide fragments contained in target protein(s) are linked in tandem;
      a DNA encoding a peptide fragment for concentration measurement conjugated with the 5' end of the tandemly linked DNA; and
      a DNA encoding a peptide fragment for concentration measurement conjugated with the 3' end of the tandemly linked DNA differing in amino acid sequence from the peptide fragment for concentration measurement encoded by the DNA conjugated with the 5' end of the tandemly linked DNA; and
   wherein the peptide fragments for concentration measurement are different in amino acid sequence from naturally occurring proteins and their variants, and detectable by a liquid chromatograph-tandem mass spectrometer (LC/MS/MS);
   (B') subjecting the stable isotope-labeled protein to digestion by trypsin to prepare stable isotope-labeled peptide fragments for concentration measurement;
   (C') quantifying the stable isotope-labeled peptide fragments for concentration measurement using LC/MS/MS;
   (D') calculating the concentration of the stable isotope-labeled target protein from the quantification value of the stable isotope-labeled peptide fragments for concentration measurement;
   (E') adding the stable isotope-labeled protein with the known concentration obtained in the step (D') to a sample comprising one or more types of target proteins, followed by digestion using trypsin to prepare target peptide fragments and stable isotope-labeled target peptide fragments with the known concentration;
   (F') using, as internal standards, the stable isotope-labeled target peptide fragments with the known concentration obtained in the step (E') to quantify the target peptide fragments obtained in the step (E') using a liquid chromatograph-tandem mass spectrometer (LC/MS/MS); and
   (G') calculating the concentration of the target protein from the quantification value of the target peptide fragments.

11. The quantification method according to claim 10, further comprising a step (p) of, before the digestion by trypsin, contacting the target proteins with antibodies capable of specifically binding to the target proteins to purify the target proteins in advance.

12. The quantification method according to claim 10, wherein the digestion by trypsin is digestion using trypsin and lysyl endopeptidase in combination.

13. The quantification method according to claim 10, wherein the peptide fragments for concentration measurement consist of the amino acid sequence represented by QIGDPTVPSGVK (SEQ ID NO: 1) or NVAPAGPTLK (SEQ ID NO: 2).

14. The quantification method according to claim 10, wherein the stable isotope-labeled protein is obtained by the expression of a DNA in which a portion of a DNA encoding ntcp protein consisting of the amino acid sequence represented by SEQ ID NO: 8 is substituted by the DNA conjugate.

15. A method for quantifying a target protein in a sample, comprising the following steps (A") to (F"):
   (A") expressing a DNA conjugate in a system having a stable isotope-labeled amino acid to thereby prepare a stable isotope-labeled protein, wherein the DNA conjugate comprises:
      a tandemly linked DNA in which two or more DNAs encoding one or more types of target peptide fragments contained in target protein(s) are linked in tandem;
      a DNA encoding a peptide fragment for concentration measurement conjugated with the 5' end of the tandemly linked DNA; and
      a DNA encoding a peptide fragment for concentration measurement conjugated with the 3' end of the tandemly linked DNA differing in amino acid sequence from the peptide fragment for concentration measurement encoded by the DNA conjugated with the 5' end of the tandemly linked DNA; and
   wherein the peptide fragments for concentration measurement are different in amino acid sequence from naturally occurring proteins and their variants, and detectable by a liquid chromatograph-tandem mass spectrometer (LC/MS/MS);
   (B") adding the stable isotope-labeled protein prepared in the step (A") to a sample comprising one or more types of target proteins, followed by digestion by trypsin to prepare target peptide fragments, stable isotope-labeled target peptide fragments, and a stable isotope-labeled peptide fragments for concentration measurement;
   (C") quantifying the stable isotope-labeled peptide fragments for concentration measurement using LC/MS/MS;
   (D") calculating the concentration of the stable isotope-labeled target peptide fragments from the quantification value of the stable isotope-labeled peptide fragments for concentration measurement;
   (E") using, as internal standards, the stable isotope-labeled target peptide fragments with the known concentration obtained in the step (D") to quantify the target peptide fragments obtained in the step (B") using LC/MS/MS; and
   (F") calculating the concentration of the target protein from the quantification value of the target peptide fragments.

16. The quantification method according to claim 15, further comprising a step (p) of, before the digestion by trypsin, contacting the target proteins with antibodies capable of specifically binding to the target proteins to purify the target proteins in advance.

17. The quantification method according to claim 15, wherein the digestion by trypsin is digestion using trypsin and lysyl endopeptidase in combination.

18. The quantification method according to claim 15, wherein the peptide fragments for concentration measurement consist of the amino acid sequence represented by QIGDPTVPSGVK (SEQ ID NO: 1) or NVAPAGPTLK (SEQ ID NO: 2).

19. The quantification method according to claim 15, wherein the stable isotope-labeled protein is obtained by the expression of a DNA in which a portion of a DNA encoding ntcp protein consisting of the amino acid sequence represented by SEQ ID NO: 8 is substituted by the DNA conjugate.

* * * * *

SEQUENCE LISTING

<160> NUMBER OF SEQ ID NOS: 52

<210> SEQ ID NO 1
<211> LENGTH: 12
<212> TYPE: PRT
<213> ORGANISM: artificial
<220> FEATURE:
<223> OTHER INFORMATION: synthesized monitoring peptide1 (evaluation peptide1)
<220> FEATURE:
<223> OTHER INFORMATION: Inventor: Ohtsuki, Sumio; Terasaki, Tetsuya

<400> SEQUENCE: 1

Gln Ile Gly Asp Pro Thr Val Pro Ser Gly Val Lys
1               5                   10

<210> SEQ ID NO 2
<211> LENGTH: 10
<212> TYPE: PRT
<213> ORGANISM: artificial
<220> FEATURE:
<223> OTHER INFORMATION: synthesized monitoring peptide2 (evaluation peptide2)

<400> SEQUENCE: 2

Asn Val Ala Pro Ala Gly Pro Thr Leu Lys
1               5                   10

<210> SEQ ID NO 3
<211> LENGTH: 10
<212> TYPE: PRT
<213> ORGANISM: artificial
<220> FEATURE:
<223> OTHER INFORMATION: synthesized monitoring peptide3 (evaluation peptide3)

<400> SEQUENCE: 3

Val Gly Ala Pro Gly Val Pro Ala Leu Lys
1               5                   10

<210> SEQ ID NO 4
<211> LENGTH: 8
<212> TYPE: PRT
<213> ORGANISM: artificial
<220> FEATURE:
<223> OTHER INFORMATION: synthesized monitoring peptide4 (evaluation peptide4)

<400> SEQUENCE: 4

Asp Ala Pro Gly Ser Gly Leu Lys 1               5

<210> SEQ ID NO 5
<211> LENGTH: 366
<212> TYPE: PRT
<213> ORGANISM: artificial
<220> FEATURE:
<223> OTHER INFORMATION: synthesized monitoring protein1 (standard
      protein1)

<400> SEQUENCE: 5

Met Glu Ala His Asn Val Ser Ala Pro Phe Asn Phe Ser Leu Pro Pro
1               5                   10                  15

Gly Phe Gly His Arg Ala Thr Asp Thr Ala Leu Ser Val Ile Leu Val
                20                  25                  30

Val Met Leu Leu Leu Ile Met Leu Ser Leu Gly Cys Thr Met Glu Phe
            35                  40                  45

Ser Lys Ile Lys Ala His Phe Trp Lys Pro Lys Gly Val Ile Ile Ala
        50                  55                  60

Ile Val Ala Gln Tyr Gly Ile Met Pro Leu Ser Ala Phe Leu Leu Gly
65                  70                  75                  80

Lys Val Phe His Leu Thr Ser Ile Glu Ala Leu Ala Ile Leu Ile Cys
                85                  90                  95

Gly Cys Ser Pro Gly Gly Asn Leu Ser Asn Leu Phe Thr Leu Ala Met
                100                 105                 110

Lys Gly Asp Met Asn Leu Ser Ile Val Met Thr Thr Cys Ser Ser Phe
            115                 120                 125

Thr Ala Leu Gly Met Met Pro Leu Leu Leu Tyr Ile Tyr Ser Lys Gln
        130                 135                 140

Ile Gly Asp Pro Thr Val Pro Ser Gly Val Lys Asp Lys Val Pro Tyr
145                 150                 155                 160

Lys Gly Ile Met Leu Ser Leu Val Met Val Leu Ile Pro Cys Ala Ile
                165                 170                 175

Gly Ile Phe Leu Lys Ser Lys Arg Pro His Tyr Val Pro Tyr Val Leu
            180                 185                 190

Lys Ala Gly Met Ile Ile Thr Phe Ser Leu Ser Val Ala Val Thr Val
        195                 200                 205

Leu Ser Val Ile Asn Val Gly Asn Ser Ile Met Phe Val Met Thr Pro
210                 215                 220

His Leu Leu Ala Thr Ser Ser Leu Met Pro Phe Thr Gly Phe Leu Met
225                 230                 235                 240

Gly Tyr Ile Leu Ser Ala Leu Phe Arg Leu Asn Pro Ser Cys Arg Arg
                245                 250                 255

Thr Ile Ser Met Glu Thr Gly Phe Gln Asn Val Gln Leu Cys Ser Thr
            260                 265                 270

Ile Leu Asn Val Thr Phe Pro Pro Glu Val Ile Gly Pro Leu Phe Phe
        275                 280                 285

Phe Pro Leu Leu Tyr Met Ile Phe Gln Leu Ala Glu Gly Leu Leu Phe
        290                 295                 300

Ile Ile Ile Phe Arg Cys Tyr Leu Lys Ile Lys Pro Gln Lys Asp Gln
305                 310                 315                 320

Thr Lys Ile Thr Tyr Lys Ala Ala Thr Glu Asp Ala Thr Pro Ala
                325                 330                 335

Ala Leu Glu Lys Gly Thr His Asn Gly Asn Asn Pro Thr Gln Pro
            340                 345                 350

Gly Leu Ser Pro Asn Gly Leu Asn Ser Gly Gln Met Ala Asn
            355                 360                 365

<210> SEQ ID NO 6
<211> LENGTH: 350
<212> TYPE: PRT
<213> ORGANISM: artificial
<220> FEATURE:
<223> OTHER INFORMATION: synthesized monitoring protein2 (standard
      protein2)

<400> SEQUENCE: 6

Ser Ser Gly Ser Ser Gly Ile Glu Gly Arg Trp Ser Lys Asn Val Ala
1               5                   10                  15

Pro Ala Gly Pro Thr Leu Lys Glu Val Gly Ser Leu Lys Pro Val
            20                  25                  30

Val Val Gln Thr Leu Arg Pro Gln Asn Val Gly Thr Arg Ile Arg Ser
            35                  40                  45

Leu Leu Pro Pro Pro Pro Ser Gly Lys Leu Lys Glu Ser Arg Gln
    50                  55                  60

Phe Lys Asn Val Ala Pro Ala Gly Pro Thr Leu Lys Thr Arg Met Gly
65                  70                  75                  80

Val Phe Thr Pro Pro Val Pro Lys Phe Ser Gln Phe Ser Val Lys
                85                  90                  95

Asn Val Ala Pro Ala Gly Pro Thr Leu Lys His Gln Asn Ala Leu Glu
            100                 105                 110

Arg Phe Tyr Asp Pro Pro Ala Gly Lys Val Leu Leu Ser Val Asp Thr
            115                 120                 125

Val Pro Val Pro Pro Lys Asp Thr Ala Met Asn Ser Met Thr Val Pro
    130                 135                 140

Val Phe Pro Lys Met Asp Thr Gly Ser Asn Lys Asn Val Ala Pro Ala
145                 150                 155                 160

Gly Pro Thr Leu Lys Gly Asp Ala Ser Tyr Lys Gln Ile Gly Asp Pro
            165                 170                 175

Thr Val Pro Ser Gly Val Lys Asp Val Lys Ser Cys Thr Tyr Pro Val
            180                 185                 190

Val Val Gln Thr Leu Arg Pro Asp Trp Glu Ser Arg Ile Arg Ser Leu
            195                 200                 205

Leu Pro Pro Pro Pro Ser Gly Lys Leu Lys Glu Tyr Asn Trp Ser
    210                 215                 220

Gln Lys Gln Ile Gly Asp Pro Thr Val Pro Ser Gly Val Lys Glu Arg
225                 230                 235                 240

Tyr Thr Thr Ile Gly Cys Lys Gln Ile Gly Asp Pro Thr Val Pro Ser
            245                 250                 255

Gly Val Lys Leu Gly Ser Ala Asn Phe Thr Pro Val Pro Lys
            260                 265                 270

Phe Glu Thr Gly Asp Leu Glu Arg Phe Tyr Asp Pro Pro Ala Gly Lys
            275                 280                 285

Val Leu Leu His Leu Asp Thr Val Pro Val Pro Pro Lys Asp Arg Asn
    290                 295                 300

Gly Tyr Ile Met Thr Val Pro Val Phe Pro Lys Met Lys Val Gln Thr
305                 310                 315                 320

Asp Cys Ile Ser Lys Gln Ile Gly Asp Pro Thr Val Pro Ser Gly Val
            325                 330                 335

Lys Trp Asn Gln Ile Glu Gly Arg Ser Ser Gly Ser Ser Gly
            340                 345                 350

<210> SEQ ID NO 7
<211> LENGTH: 8
<212> TYPE: PRT
<213> ORGANISM: Mus musculus

<400> SEQUENCE: 7

Gly Ile Tyr Asp Gly Asp Leu Lys
1               5

<210> SEQ ID NO 8
<211> LENGTH: 362
<212> TYPE: PRT
<213> ORGANISM: Mus musculus

<400> SEQUENCE: 8

Met Glu Ala His Asn Val Ser Ala Pro Phe Asn Phe Ser Leu Pro Pro
1               5                   10                  15

Gly Phe Gly His Arg Ala Thr Asp Thr Ala Leu Ser Val Ile Leu Val
            20                  25                  30

Val Met Leu Leu Leu Ile Met Leu Ser Leu Gly Cys Thr Met Glu Phe
        35                  40                  45

Ser Lys Ile Lys Ala His Phe Trp Lys Pro Lys Gly Val Ile Ile Ala
    50                  55                  60

Ile Val Ala Gln Tyr Gly Ile Met Pro Leu Ser Ala Phe Leu Leu Gly
65                  70                  75                  80

Lys Val Phe His Leu Thr Ser Ile Glu Ala Leu Ala Ile Leu Ile Cys
                85                  90                  95

Gly Cys Ser Pro Gly Gly Asn Leu Ser Asn Leu Phe Thr Leu Ala Met
            100                 105                 110

Lys Gly Asp Met Asn Leu Ser Ile Val Met Thr Thr Cys Ser Ser Phe
        115                 120                 125

Thr Ala Leu Gly Met Met Pro Leu Leu Leu Tyr Ile Tyr Ser Lys Gly
    130                 135                 140

Ile Tyr Asp Gly Asp Leu Lys Asp Lys Val Pro Tyr Lys Gly Ile Met
145                 150                 155                 160

Leu Ser Leu Val Met Val Leu Ile Pro Cys Ala Ile Gly Ile Phe Leu
                165                 170                 175

Lys Ser Lys Arg Pro His Tyr Val Pro Tyr Val Leu Lys Ala Gly Met
            180                 185                 190

Ile Ile Thr Phe Ser Leu Ser Val Ala Val Thr Val Leu Ser Val Ile
        195                 200                 205

Asn Val Gly Asn Ser Ile Met Phe Val Met Thr Pro His Leu Leu Ala
    210                 215                 220

Thr Ser Ser Leu Met Pro Phe Thr Gly Phe Leu Met Gly Tyr Ile Leu
225                 230                 235                 240

Ser Ala Leu Phe Arg Leu Asn Pro Ser Cys Arg Arg Thr Ile Ser Met
                245                 250                 255

Glu Thr Gly Phe Gln Asn Val Gln Leu Cys Ser Thr Ile Leu Asn Val
            260                 265                 270

Thr Phe Pro Pro Glu Val Ile Gly Pro Leu Phe Phe Phe Pro Leu Leu
        275                 280                 285

Tyr Met Ile Phe Gln Leu Ala Glu Gly Leu Leu Phe Ile Ile Ile Phe
    290                 295                 300

Arg Cys Tyr Leu Lys Ile Lys Pro Gln Lys Asp Gln Thr Lys Ile Thr
305                 310                 315                 320

```
Tyr Lys Ala Ala Ala Thr Glu Asp Ala Thr Pro Ala Ala Leu Glu Lys
                325                 330                 335

Gly Thr His Asn Gly Asn Asn Pro Pro Thr Gln Pro Gly Leu Ser Pro
            340                 345                 350

Asn Gly Leu Asn Ser Gly Gln Met Ala Asn
        355                 360

<210> SEQ ID NO 9
<211> LENGTH: 8
<212> TYPE: PRT
<213> ORGANISM: Homo sapiens

<400> SEQUENCE: 9

Glu Leu Ile Ile Glu Phe Ser Lys
1               5

<210> SEQ ID NO 10
<211> LENGTH: 6
<212> TYPE: PRT
<213> ORGANISM: Homo sapiens

<400> SEQUENCE: 10

Ile Thr Asp Phe Gly Arg
1               5

<210> SEQ ID NO 11
<211> LENGTH: 8
<212> TYPE: PRT
<213> ORGANISM: Homo sapiens

<400> SEQUENCE: 11

Ile Thr Asp Phe Gly Leu Ala Lys
1               5

<210> SEQ ID NO 12
<211> LENGTH: 9
<212> TYPE: PRT
<213> ORGANISM: Homo sapiens

<400> SEQUENCE: 12

Ser Ser Asp Tyr Phe Gly Asn Gly Arg
1               5

<210> SEQ ID NO 13
<211> LENGTH: 8
<212> TYPE: PRT
<213> ORGANISM: Homo sapiens

<400> SEQUENCE: 13

Ile Tyr Val Ser Asp Asp Gly Lys
1               5

<210> SEQ ID NO 14
<211> LENGTH: 11
<212> TYPE: PRT
<213> ORGANISM: Homo sapiens

<400> SEQUENCE: 14

Gln Gly Leu Leu Pro Val Leu Glu Ser Phe Lys
1               5                   10

<210> SEQ ID NO 15
<211> LENGTH: 11
```

```
<212> TYPE: PRT
<213> ORGANISM: Homo sapiens

<400> SEQUENCE: 15

Asp Leu Ala Thr Val Tyr Val Asp Val Leu Lys
1               5                   10

<210> SEQ ID NO 16
<211> LENGTH: 9
<212> TYPE: PRT
<213> ORGANISM: Homo sapiens

<400> SEQUENCE: 16

Ser Pro Glu Leu Gln Ala Glu Ala Lys
1               5

<210> SEQ ID NO 17
<211> LENGTH: 10
<212> TYPE: PRT
<213> ORGANISM: Homo sapiens

<400> SEQUENCE: 17

Ile Glu Ile Pro Leu Pro Phe Gly Gly Lys
1               5                   10

<210> SEQ ID NO 18
<211> LENGTH: 11
<212> TYPE: PRT
<213> ORGANISM: Homo sapiens

<400> SEQUENCE: 18

Glu Phe Gln Val Pro Thr Phe Thr Ile Pro Lys
1               5                   10

<210> SEQ ID NO 19
<211> LENGTH: 12
<212> TYPE: PRT
<213> ORGANISM: Homo sapiens

<400> SEQUENCE: 19

Asn Pro Asn Gly Tyr Ser Phe Ser Ile Pro Val Lys
1               5                   10

<210> SEQ ID NO 20
<211> LENGTH: 9
<212> TYPE: PRT
<213> ORGANISM: Homo sapiens

<400> SEQUENCE: 20

Asn Ile Ile Leu Pro Val Tyr Asp Lys
1               5

<210> SEQ ID NO 21
<211> LENGTH: 9
<212> TYPE: PRT
<213> ORGANISM: Homo sapiens

<400> SEQUENCE: 21

Thr Tyr Leu Pro Ala Val Asp Glu Lys
1               5

<210> SEQ ID NO 22
<211> LENGTH: 11
<212> TYPE: PRT
<213> ORGANISM: Homo sapiens
```

<400> SEQUENCE: 22

Gly Trp Val Thr Asp Gly Phe Ser Ser Leu Lys
1               5                   10

<210> SEQ ID NO 23
<211> LENGTH: 9
<212> TYPE: PRT
<213> ORGANISM: Homo sapiens

<400> SEQUENCE: 23

Leu Gly Pro Leu Val Glu Gln Gly Arg
1               5

<210> SEQ ID NO 24
<211> LENGTH: 12
<212> TYPE: PRT
<213> ORGANISM: Homo sapiens

<400> SEQUENCE: 24

Ile Thr Trp Ser Asn Pro Pro Ala Gln Gly Ala Arg
1               5                   10

<210> SEQ ID NO 25
<211> LENGTH: 11
<212> TYPE: PRT
<213> ORGANISM: Homo sapiens

<400> SEQUENCE: 25

Leu Ala Leu Gly Asp Asp Ser Pro Ala Leu Lys
1               5                   10

<210> SEQ ID NO 26
<211> LENGTH: 14
<212> TYPE: PRT
<213> ORGANISM: Homo sapiens

<400> SEQUENCE: 26

Phe Val Thr Val Gln Thr Ile Ser Gly Thr Gly Ala Leu Arg
1               5                   10

<210> SEQ ID NO 27
<211> LENGTH: 8
<212> TYPE: PRT
<213> ORGANISM: Homo sapiens

<400> SEQUENCE: 27

Ile Leu Val Ser Gly Gly Gly Lys
1               5

<210> SEQ ID NO 28
<211> LENGTH: 7
<212> TYPE: PRT
<213> ORGANISM: Homo sapiens

<400> SEQUENCE: 28

Thr Pro Ser Ser Trp Gly Arg
1               5

<210> SEQ ID NO 29
<211> LENGTH: 9
<212> TYPE: PRT
<213> ORGANISM: Homo sapiens

<400> SEQUENCE: 29

```
Leu Val Ile Ile Thr Ala Gly Ala Arg
1               5

<210> SEQ ID NO 30
<211> LENGTH: 9
<212> TYPE: PRT
<213> ORGANISM: Homo sapiens

<400> SEQUENCE: 30

Ile Val Val Val Thr Ala Gly Val Arg
1               5

<210> SEQ ID NO 31
<211> LENGTH: 8
<212> TYPE: PRT
<213> ORGANISM: Homo sapiens

<400> SEQUENCE: 31

Phe Pro Phe Val Ala Leu Ser Lys
1               5

<210> SEQ ID NO 32
<211> LENGTH: 10
<212> TYPE: PRT
<213> ORGANISM: Homo sapiens

<400> SEQUENCE: 32

Leu Phe Gln Pro Ser Ile Gln Leu Ala Arg
1               5                   10

<210> SEQ ID NO 33
<211> LENGTH: 12
<212> TYPE: PRT
<213> ORGANISM: Homo sapiens

<400> SEQUENCE: 33

Gly Gly Leu Ser Val Ala Val Pro Gly Glu Ile Arg
1               5                   10

<210> SEQ ID NO 34
<211> LENGTH: 11
<212> TYPE: PRT
<213> ORGANISM: Homo sapiens

<400> SEQUENCE: 34

Glu Pro Gln Val Tyr Thr Leu Pro Pro Ser Arg
1               5                   10

<210> SEQ ID NO 35
<211> LENGTH: 8
<212> TYPE: PRT
<213> ORGANISM: Homo sapiens

<400> SEQUENCE: 35

Ala Leu Pro Ala Pro Ile Glu Lys
1               5

<210> SEQ ID NO 36
<211> LENGTH: 10
<212> TYPE: PRT
<213> ORGANISM: Homo sapiens

<400> SEQUENCE: 36

Asn Ile Ala Ala Phe Gly Gly Asn Pro Lys
```

<210> SEQ ID NO 37
<211> LENGTH: 8
<212> TYPE: PRT
<213> ORGANISM: Homo sapiens

<400> SEQUENCE: 37

Phe Trp Thr Ser Phe Phe Pro Lys
1               5

<210> SEQ ID NO 38
<211> LENGTH: 16
<212> TYPE: PRT
<213> ORGANISM: Homo sapiens

<400> SEQUENCE: 38

Ile Asn Gly Ile Pro Gln Gln His Thr Gln Val Leu Phe Ile Ala Lys
1               5                   10                  15

<210> SEQ ID NO 39
<211> LENGTH: 12
<212> TYPE: PRT
<213> ORGANISM: Homo sapiens

<400> SEQUENCE: 39

His Ser Gln Pro Trp Gln Val Leu Val Ala Ser Arg
1               5                   10

<210> SEQ ID NO 40
<211> LENGTH: 11
<212> TYPE: PRT
<213> ORGANISM: Homo sapiens

<400> SEQUENCE: 40

Leu Thr Ser Pro Val Val Thr Thr Ser Thr Arg
1               5                   10

<210> SEQ ID NO 41
<211> LENGTH: 11
<212> TYPE: PRT
<213> ORGANISM: Homo sapiens

<400> SEQUENCE: 41

Phe Pro Asp Ile Phe Ser Val Ala Ser Ser Arg
1               5                   10

<210> SEQ ID NO 42
<211> LENGTH: 9
<212> TYPE: PRT
<213> ORGANISM: Homo sapiens

<400> SEQUENCE: 42

Ser Ser Val Pro Ser Ser Thr Glu Lys
1               5

<210> SEQ ID NO 43
<211> LENGTH: 8
<212> TYPE: PRT
<213> ORGANISM: Homo sapiens

<400> SEQUENCE: 43

Ala Thr Thr Thr Pro Ala Ser Lys
1               5

<210> SEQ ID NO 44
<211> LENGTH: 10
<212> TYPE: PRT
<213> ORGANISM: Homo sapiens

<400> SEQUENCE: 44

Ile Leu Gly Ala Thr Ile Glu Asn Ser Arg
1               5                   10

<210> SEQ ID NO 45
<211> LENGTH: 9
<212> TYPE: PRT
<213> ORGANISM: Homo sapiens

<400> SEQUENCE: 45

Ala Asn Thr Phe Leu Glu Glu Val Arg
1               5

<210> SEQ ID NO 46
<211> LENGTH: 7
<212> TYPE: PRT
<213> ORGANISM: Homo sapiens

<400> SEQUENCE: 46

Val Leu Gln Gly Leu Pro Arg
1               5

<210> SEQ ID NO 47
<211> LENGTH: 7
<212> TYPE: PRT
<213> ORGANISM: Homo sapiens

<400> SEQUENCE: 47

Gly Gly Val Leu Ile Gln Arg
1               5

<210> SEQ ID NO 48
<211> LENGTH: 7
<212> TYPE: PRT
<213> ORGANISM: Escherichia coli

<400> SEQUENCE: 48

Gln Ile Asp Ala Val Leu Lys
1               5

<210> SEQ ID NO 49
<211> LENGTH: 433
<212> TYPE: PRT
<213> ORGANISM: Artificial
<220> FEATURE:
<223> OTHER INFORMATION: synthesized model protein 1

<400> SEQUENCE: 49

Met Trp Ser His Pro Gln Phe Glu Lys Gln Ile Gly Asp Pro Thr Val
1               5                   10                  15

Pro Ser Gly Val Lys Ser Ser Gly Ser Ser Gly Arg Leu Glu Leu Pro
            20                  25                  30

Leu Asp Arg Asp Leu Leu Ser Gly Val Asn Lys Glu Gln Phe Gln Glu
        35                  40                  45

Ala Val Pro Gly Arg Leu Val Glu Ala Gly Glu Val Asp Pro Asp Pro
    50                  55                  60

Gly Asn Asn Lys Tyr Ile Leu Pro Pro Val Val Lys Ala Phe Pro Val
65                  70                  75                  80

```
Ser His Tyr Arg Gln Asn Glu Ile Asn Lys Gly Gln Glu Gln Thr Pro
                85                  90                  95

Gly Glu Gly Phe Ile Gln Val Arg Ile Pro Asp Glu Asp Glu Ser Glu
            100                 105                 110

Val Thr Ser Ser Ala Ser Glu Lys Ala Val Gly Tyr Pro Gly Ala Pro
        115                 120                 125

Pro Pro Ala Ala Asp Phe Lys Ile Ser Thr Gly Pro Leu Gly Asp Leu
    130                 135                 140

Ser Arg Ser Ile Pro Gly Val Ala Ile Asp Gly Glu Asn Asn Met Arg
145                 150                 155                 160

Ile Ser Pro Leu Gln Ala Asn Asn Gln Gln Val Ile Arg Tyr Pro
                165                 170                 175

Ile Val Glu Gln Tyr Leu Lys Leu Pro Ser Val Gln Leu Gln Arg Asn
            180                 185                 190

His Pro Asn His Ala Leu Lys Val Ser Val Pro Asn Phe Gly Arg Ile
        195                 200                 205

Ser Val Ala Glu Asp Gly Arg Tyr Gly Ile Glu Glu His Gly Lys Pro
    210                 215                 220

Asp Gln Ile Gln Tyr Thr Glu Leu Ser Asn Ala Lys Ala His Asp Gln
225                 230                 235                 240

Asn Leu Ala Asn Leu Ala Leu Gln Ala Leu Arg Leu Glu Leu Pro Leu
                245                 250                 255

Asp Lys Ser Ile Asn Gln Asp Cys Ile Leu Gln Lys Asp Thr Thr Asp
            260                 265                 270

Glu Leu Ser Val Val Glu Ala Lys Gly Asp Pro Asp Pro Phe Gly Pro
        275                 280                 285

Pro Ala Tyr Ala His Arg Gly Gly His Pro Gln Asp Glu Ser Val Ile
    290                 295                 300

Leu Thr Lys Leu Leu Glu Ser Gly Asp Pro Glu Ala Asp Pro Ala Ser
305                 310                 315                 320

Glu Lys Val Trp Gly Asp Asp Gln Lys His Ser Thr Ala Ile Gly Arg
                325                 330                 335

His Leu Glu Thr Ile Ala Gly Glu Gln Phe Lys Glu Thr Ser Leu Asp
            340                 345                 350

Leu Gly Gly Lys Thr Gly Ala Tyr Glu Tyr Pro Val Ala Glu Lys Gln
        355                 360                 365

Val Ala Glu Gln Gln Thr Pro Ala Ser Lys Pro Phe Ser Gln Phe Glu
    370                 375                 380

Glu Lys Ile Ser Leu Leu Gln Ala Asn Asn Lys Glu Phe Ser Ala Ser
385                 390                 395                 400

Ser Gly Ser Ser Lys Asn Val Ala Pro Ala Gly Pro Thr Leu Lys Asp
                405                 410                 415

His Leu Ile His Asn Val His Lys Glu Glu His Ala His Ala His Asn
            420                 425                 430

Lys

<210> SEQ ID NO 50
<211> LENGTH: 467
<212> TYPE: PRT
<213> ORGANISM: Artificial
<220> FEATURE:
<223> OTHER INFORMATION: synthesized model protein 2

<400> SEQUENCE: 50
```

```
Met Trp Ser His Pro Gln Phe Glu Lys Gln Ile Gly Asp Pro Thr Val
  1               5                  10                  15

Pro Ser Gly Val Lys Ser Gly Ser Arg Trp Leu Ala Glu Ser Ala
             20                  25                  30

Arg Ala Tyr Val Pro Ile Ala Gln Val Lys Thr Glu Leu Glu Ser Thr
                 35                  40                  45

Ile Phe Gly Ser Pro Arg Phe Ser Asn Ser Gly Ser Arg Asp Ala Val
 50                      55                  60

Thr Thr Thr Val Thr Gly Ala Lys Phe Gly Thr Pro Val Gln Glu
 65                  70                  75                  80

Arg Ser Ile Thr Val Phe Phe Lys Phe Gly Gln Thr Pro Val Gln Glu
                 85                  90                  95

Arg Leu Val Gly Leu Glu Ala Pro Ser Val Arg Phe Val His Pro Gln
                100                 105                 110

Trp Lys Ala Val Phe Phe Pro Gly Asn Gln Glu Lys Thr Val Thr Gly
            115                 120                 125

Thr Val Lys Tyr Gln Tyr Tyr Ser Asn Lys Ser Val Val Ser Gly Ser
        130                 135                 140

Ile Asn Thr Val Leu Gly Ser Arg Tyr Gln Tyr Asn Thr Asp Val Val
145                 150                 155                 160

Phe Asp Ser Gln Gly Lys Asp Leu His Asp Ala Asn Thr Asp Leu Ile
                165                 170                 175

Gly Arg Tyr Gln Tyr Asn Thr Asp Val Val Phe Asp Ser Gln Gly Lys
            180                 185                 190

Ala Ile Val Pro Glu Ser Lys Tyr Phe Thr Trp Asp Glu Val Ala Gln
        195                 200                 205

Arg Tyr Phe Thr Trp Asp Glu Val Ala Gln Arg Thr Ile Pro Ser Val
210                 215                 220

Asp Asp Phe Gln Asn Tyr Leu Arg Phe Tyr Thr Ala Pro Thr Ala Ile
225                 230                 235                 240

Arg Ala Pro Asn Asn Phe Thr Ile Gln Asn Gln Tyr Pro Arg Gln Gly
                245                 250                 255

Glu Leu Ser Pro Val Glu Asp Gln Arg Tyr Gly Pro Leu Gln Glu Leu
                260                 265                 270

Glu Glu Thr Ala Ala Arg Val Phe Phe Ala Ser Asp Pro Ile Lys Glu
            275                 280                 285

Ser Asp Thr Ser Tyr Val Ser Leu Lys Gln Thr Ser Ile Leu Ile Gln
        290                 295                 300

Lys Val Ser Ile Gly Arg Glu Ser Gly Gln Leu Trp Leu Asp Ala Tyr
305                 310                 315                 320

Leu His Gln Glu Ser Gly Gln Leu Trp Leu Asp Ala Tyr Leu His Gln
                325                 330                 335

Leu Ile Asp Thr Ile Ala Ser Glu Ile Gly Glu Leu Lys Asp Gln Asp
            340                 345                 350

Gly Tyr Tyr Trp Ile Thr Gly Arg Leu Thr Glu Asn Thr Thr Leu
        355                 360                 365

Arg Asp Pro Gln Asp Pro Ser Gly Arg Leu Ile Pro Asp Glu Asn Pro
370                 375                 380

Ser Ser Phe Ser Gly Leu Ile Arg Gly Ile Gly Leu Phe Ile Gly
385                 390                 395                 400

Ile Asp Leu Val Lys Ala Pro Leu Thr Lys Pro Leu Lys Leu Ile Pro
                405                 410                 415

Asp Glu Asn Pro Ser Ser Phe Ser Gly Asn Leu Ile Arg Glu Phe Ser
```

```
                    420              425              430
Ala Ser Ser Gly Ser Ser Lys Asn Val Ala Pro Ala Gly Pro Thr Leu
                435              440              445

Lys Asp His Leu Ile His Asn Val His Lys Glu Glu His Ala His Ala
450              455              460

His Asn Lys
465

<210> SEQ ID NO 51
<211> LENGTH: 367
<212> TYPE: PRT
<213> ORGANISM: Artificial
<220> FEATURE:
<223> OTHER INFORMATION: synthesized tandemly linked protein1

<400> SEQUENCE: 51

Leu Glu Leu Pro Leu Asp Arg Asp Leu Leu Ser Gly Val Asn Lys Glu
1               5                   10                  15

Gln Phe Gln Glu Ala Val Pro Gly Arg Leu Val Glu Ala Gly Glu Val
                20                  25                  30

Asp Pro Asp Pro Gly Asn Asn Lys Tyr Ile Leu Pro Pro Val Val Lys
            35                  40                  45

Ala Phe Pro Val Ser His Tyr Arg Gln Asn Glu Ile Asn Lys Gly Gln
        50                  55                  60

Glu Gln Thr Pro Gly Glu Gly Phe Ile Gln Val Arg Ile Pro Asp Glu
65                  70                  75                  80

Asp Glu Ser Glu Val Thr Ser Ser Ala Ser Gly Lys Ala Val Gly Tyr
                85                  90                  95

Pro Gly Ala Pro Pro Ala Ala Asp Phe Lys Ile Ser Thr Gly Pro
                100                 105                 110

Leu Gly Asp Leu Ser Arg Ser Ile Pro Gly Val Ala Ile Asp Gly Glu
            115                 120                 125

Asn Asn Met Arg Ile Ser Pro Leu Gln Ala Asn Gln Gln Gln Val
        130                 135                 140

Ile Arg Tyr Pro Ile Val Glu Gln Tyr Leu Lys Leu Pro Ser Val Gln
145                 150                 155                 160

Leu Gln Arg Asn His Pro Asn His Ala Leu Lys Val Ser Val Pro Asn
                165                 170                 175

Phe Gly Arg Ile Ser Val Ala Glu Asp Gly Arg Tyr Gly Ile Glu Glu
            180                 185                 190

His Gly Lys Pro Asp Gln Ile Gln Tyr Thr Glu Leu Ser Asn Ala Lys
        195                 200                 205

Ala His Asp Gln Asn Leu Ala Asn Leu Ala Leu Gln Ala Leu Arg Leu
    210                 215                 220

Glu Leu Pro Leu Asp Lys Ser Ile Asn Gln Asp Cys Ile Leu Gln Lys
225                 230                 235                 240

Asp Thr Thr Asp Glu Leu Ser Val Val Glu Ala Lys Gly Asp Pro Asp
                245                 250                 255

Pro Phe Gly Pro Pro Ala Tyr Ala His Arg Gly Gly His Pro Gln Asp
            260                 265                 270

Glu Ser Val Ile Leu Thr Lys Leu Leu Glu Ser Gly Asp Pro Glu Ala
        275                 280                 285

Asp Pro Ala Ser Glu Lys Val Trp Gly Asp Asp Gln Lys His Ser Thr
    290                 295                 300

Ala Ile Gly Arg His Leu Glu Thr Ile Ala Gly Glu Gln Phe Lys Glu
```

```
                305                 310                 315                 320
Thr Ser Leu Asp Leu Gly Gly Lys Thr Gly Ala Tyr Glu Tyr Pro Val
                    325                 330                 335

Ala Glu Lys Gln Val Ala Glu Gln Gln Thr Pro Ala Ser Lys Pro Phe
                340                 345                 350

Ser Gln Phe Glu Glu Lys Ile Ser Leu Leu Gln Ala Asn Asn Lys
            355                 360                 365

<210> SEQ ID NO 52
<211> LENGTH: 403
<212> TYPE: PRT
<213> ORGANISM: Artificial
<220> FEATURE:
<223> OTHER INFORMATION: synthesized tandemly linked protein2

<400> SEQUENCE: 52

Trp Leu Ala Glu Ser Ala Arg Ala Tyr Val Pro Ile Ala Gln Val Lys
1               5                   10                  15

Thr Glu Leu Glu Ser Thr Ile Phe Gly Ser Pro Arg Phe Ser Asn Ser
                20                  25                  30

Gly Ser Arg Asp Ala Val Thr Thr Val Thr Gly Ala Lys Phe Gly
            35                  40                  45

Gln Thr Pro Val Gln Glu Arg Ser Ile Thr Val Phe Phe Lys Phe Gly
50                  55                  60

Gln Thr Pro Val Gln Glu Arg Leu Val Gly Leu Glu Ala Pro Ser Val
65                  70                  75                  80

Arg Phe Val His Pro Gln Trp Lys Ala Val Phe Phe Pro Gly Asn Gln
                85                  90                  95

Glu Lys Thr Val Thr Gly Thr Val Lys Tyr Gln Tyr Tyr Ser Asn Lys
                100                 105                 110

Ser Val Val Ser Gly Ser Ile Asn Thr Val Leu Gly Ser Arg Tyr Gln
            115                 120                 125

Tyr Asn Thr Asp Val Val Phe Asp Ser Gln Gly Lys Asp Leu His Asp
    130                 135                 140

Ala Asn Thr Asp Leu Ile Gly Arg Tyr Gln Tyr Asn Thr Asp Val Val
145                 150                 155                 160

Phe Asp Ser Gln Gly Lys Ala Ile Val Pro Glu Ser Lys Tyr Phe Thr
                165                 170                 175

Trp Asp Glu Val Ala Gln Arg Tyr Phe Thr Trp Asp Glu Val Ala Gln
            180                 185                 190

Arg Thr Ile Pro Ser Val Asp Asp Phe Gln Asn Tyr Leu Arg Phe Tyr
    195                 200                 205

Thr Ala Pro Thr Ala Ile Arg Ala Pro Asn Asn Phe Thr Ile Gln Asn
210                 215                 220

Gln Tyr Pro Arg Gln Gly Glu Leu Ser Pro Val Glu Asp Gln Arg Tyr
225                 230                 235                 240

Gly Pro Leu Gln Glu Leu Glu Glu Thr Ala Ala Arg Val Phe Phe Ala
                245                 250                 255

Ser Asp Pro Ile Lys Glu Ser Asp Thr Ser Tyr Val Ser Leu Lys Gln
            260                 265                 270

Thr Ser Ile Leu Ile Gln Lys Val Ser Ile Gly Arg Glu Ser Gly Gln
    275                 280                 285

Leu Trp Leu Asp Ala Tyr Leu His Gln Glu Ser Gly Gln Leu Trp Leu
290                 295                 300

Asp Ala Tyr Leu His Gln Leu Ile Asp Thr Ile Ala Ser Glu Ile Gly
```

```
                    305                 310                 315                 320
                Glu Leu Lys Asp Gln Asp Gly Tyr Tyr Trp Ile Thr Gly Arg Leu Thr
                                325                 330                 335

Glu Glu Asn Thr Thr Leu Arg Asp Pro Gln Asp Pro Ser Gly Arg Leu
                                340                 345                 350

Ile Pro Asp Glu Asn Pro Ser Ser Phe Ser Gly Ser Leu Ile Arg Gly
                                355                 360                 365

Ile Gly Leu Phe Ile Gly Ile Asp Leu Val Lys Ala Pro Leu Thr Lys
                                370                 375                 380

Pro Leu Lys Leu Ile Pro Asp Glu Asn Pro Ser Ser Phe Ser Gly Asn
                385                 390                 395                 400

Leu Ile Arg
```